US009289582B2

(12) United States Patent
Suehara

(10) Patent No.: US 9,289,582 B2
(45) Date of Patent: Mar. 22, 2016

(54) METHODS FOR TREATING SINUS OSTIA USING BALLOON CATHETER DEVICES HAVING A BENDABLE BALLOON PORTION

(71) Applicant: Terumo Kabushiki Kaisha, Kanagawa (JP)

(72) Inventor: Satoru Suehara, Kanagawa (JP)

(73) Assignee: TERUMO KABUSHIKI KAISHA, Kanagawa (JP)

( * ) Notice: Subject to any disclaimer, the term of this patent is extended or adjusted under 35 U.S.C. 154(b) by 424 days.

(21) Appl. No.: 13/776,057

(22) Filed: Feb. 25, 2013

(65) Prior Publication Data
US 2014/0243876 A1 Aug. 28, 2014

(51) Int. Cl.
| A61M 29/02 | (2006.01) |
| A61B 17/24 | (2006.01) |
| A61B 1/00 | (2006.01) |
| A61B 1/233 | (2006.01) |
| A61M 25/01 | (2006.01) |
| A61B 19/00 | (2006.01) |
| A61B 17/00 | (2006.01) |

(Continued)

(52) U.S. Cl.
CPC ............ A61M 29/02 (2013.01); A61B 1/00082 (2013.01); A61B 1/00087 (2013.01); A61B 1/233 (2013.01); A61B 17/24 (2013.01); A61M 25/0138 (2013.01); A61B 1/05 (2013.01); A61B 1/0676 (2013.01); A61B 1/0684 (2013.01); A61B 19/5212 (2013.01); A61B 2017/003 (2013.01); A61B 2019/521 (2013.01); A61M 25/0133 (2013.01); A61M 25/0136 (2013.01); A61M 2210/0681 (2013.01)

(58) Field of Classification Search
CPC ............... A61M 2210/0681; A61M 25/0133; A61M 29/00; A61M 29/02; A61M 2029/025; A61B 1/00082; A61B 1/05; A61B 1/0676; A61B 1/233; A61B 17/24; A61B 2018/00327
See application file for complete search history.

(56) References Cited

U.S. PATENT DOCUMENTS

| 4,961,738 A | 10/1990 | Mackin |
| 5,624,380 A | 4/1997 | Takayama et al. |
| 2005/0085693 A1 | 4/2005 | Belson et al. |

(Continued)

FOREIGN PATENT DOCUMENTS

WO    WO 2006/034008 A2    3/2006

OTHER PUBLICATIONS

US Office Action, U.S. Appl. No. 13/840,607 issued Jul. 6, 2015.

Primary Examiner — Eric Rosen
Assistant Examiner — Todd J Scherbel
(74) Attorney, Agent, or Firm — Foley & Lardner LLP

(57) ABSTRACT

A method for use with a balloon catheter device that includes a selectively bendable portion with a balloon disposed thereon, a control device for controlling bending of the selectively bendable portion, and a camera located at an end of a distal portion, includes inserting the distal portion into the nostril while the distal portion is straight; viewing an image provided by the camera; stopping insertion of the distal portion after the ethmoidal bulla is viewed in the image; articulating the distal portion in an upward direction to view the opening to the frontal sinus ostium or a downward direction to view the opening to the maxillary sinus ostium using the control device; inserting the distal portion into the frontal sinus ostium or the maxillary sinus ostium while the distal portion remains in the bent position; and inflating the balloon in the frontal sinus ostium or the maxillary sinus ostium.

16 Claims, 21 Drawing Sheets

(51) Int. Cl.
  *A61B 1/05* (2006.01)
  *A61B 1/06* (2006.01)

(56) References Cited

U.S. PATENT DOCUMENTS

| | | | |
|---|---|---|---|
| 2005/0240147 A1* | 10/2005 | Makower et al. | 604/96.01 |
| 2006/0210605 A1 | 9/2006 | Chang et al. | |
| 2007/0073269 A1* | 3/2007 | Becker | 604/509 |
| 2008/0097159 A1 | 4/2008 | Ishiguro | |
| 2009/0187098 A1 | 7/2009 | Makower et al. | |
| 2012/0253123 A1* | 10/2012 | Shimizu et al. | 600/116 |
| 2012/0259217 A1 | 10/2012 | Gerrans et al. | |
| 2013/0030458 A1 | 1/2013 | Drontle et al. | |
| 2013/0066358 A1* | 3/2013 | Nalluri et al. | 606/199 |

* cited by examiner

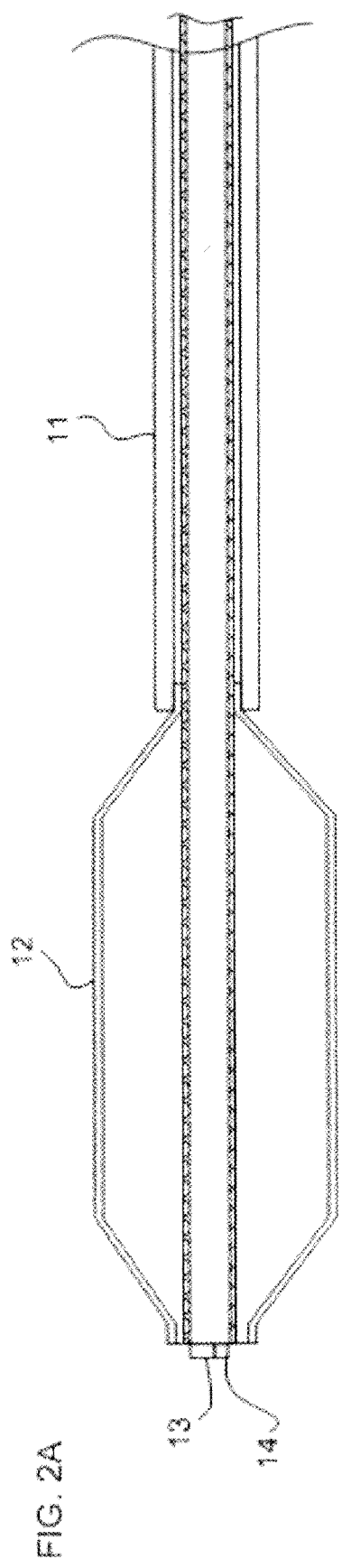
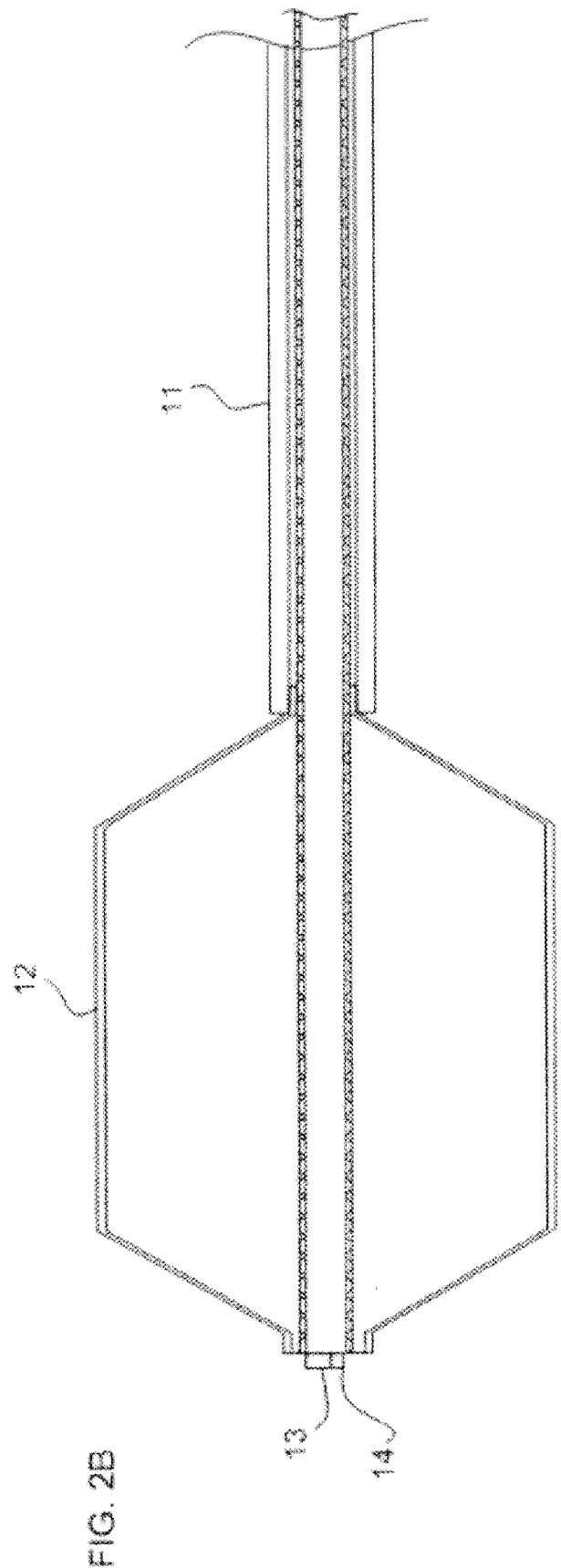

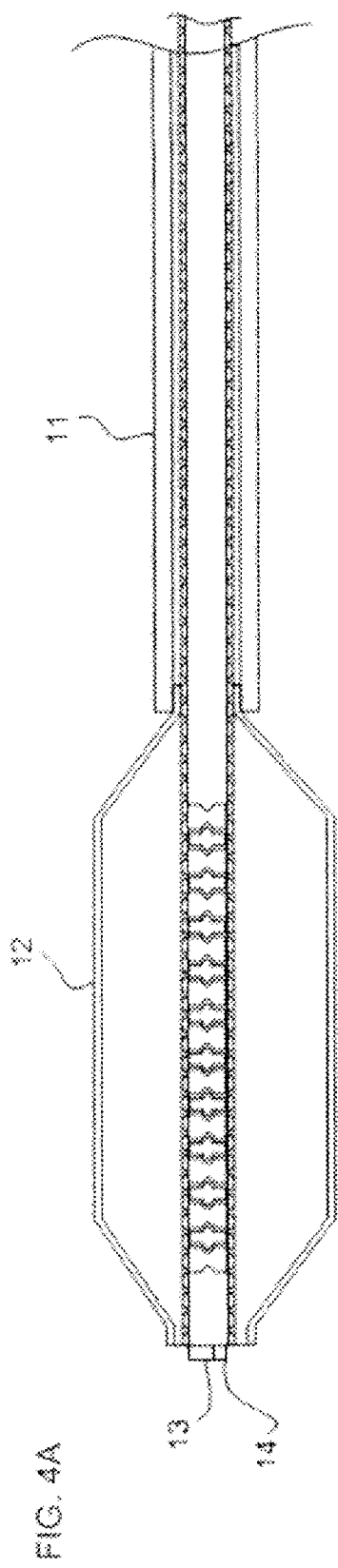
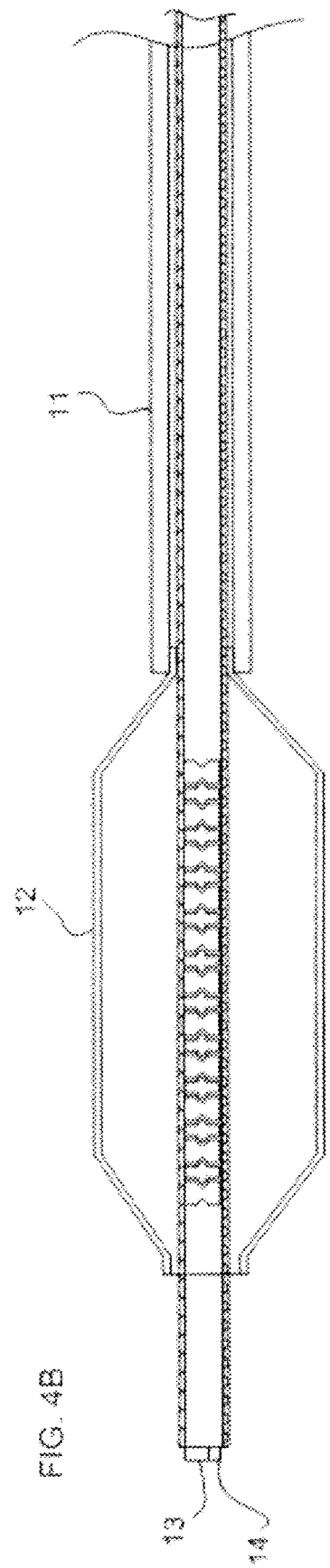

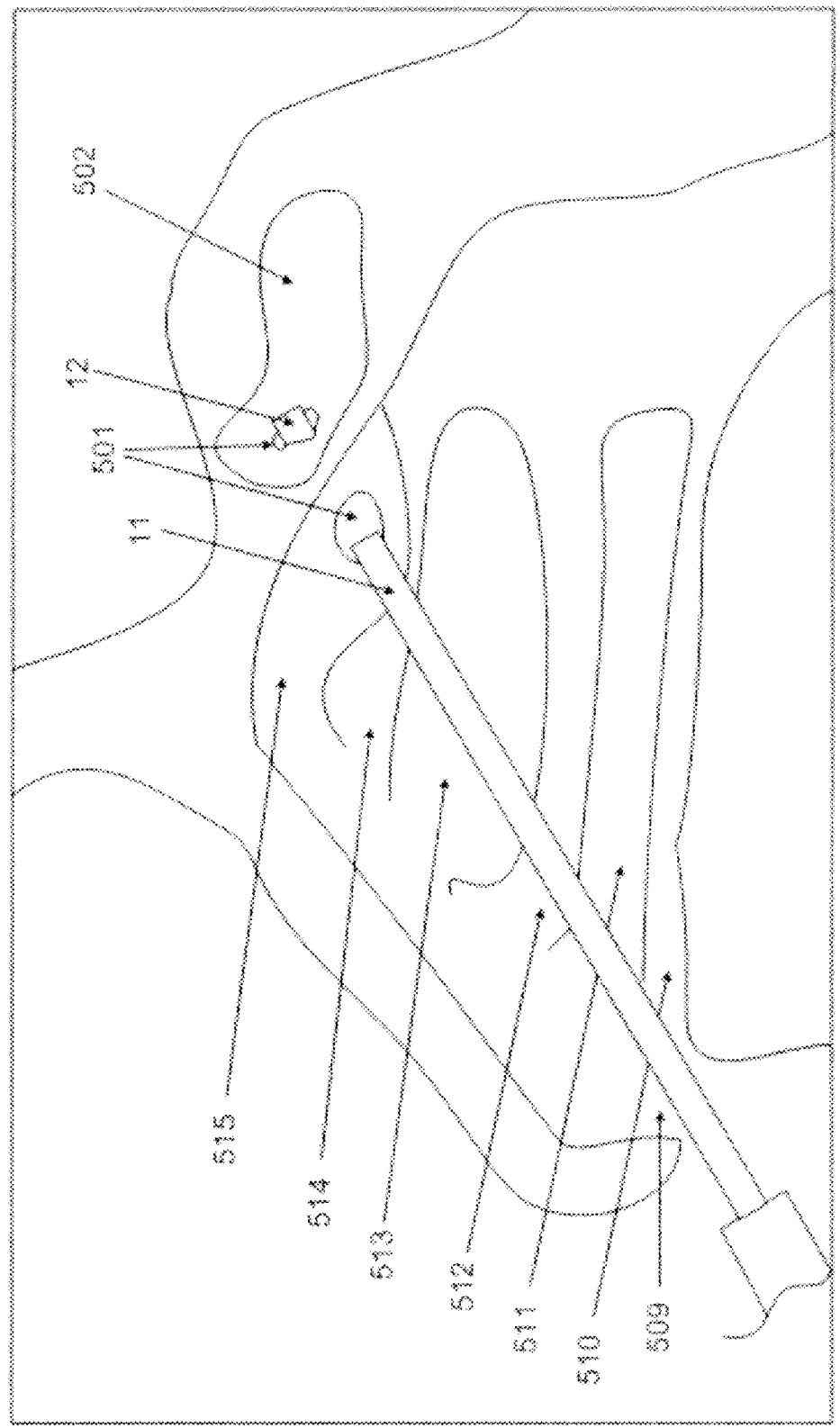

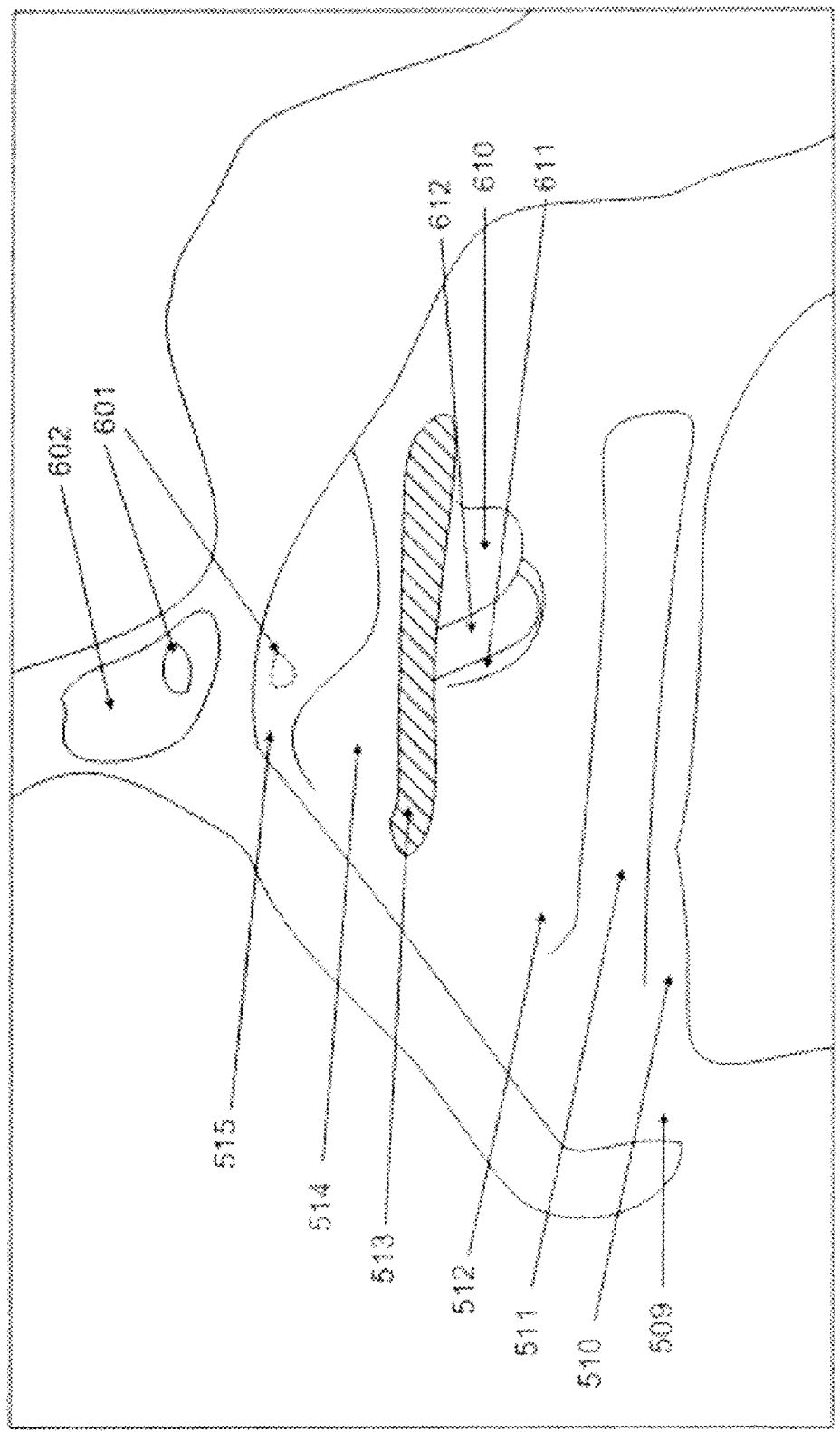

METHODS FOR TREATING SINUS OSTIA USING BALLOON CATHETER DEVICES HAVING A BENDABLE BALLOON PORTION

BACKGROUND

1. Technical Field

The present disclosure relates to an otorhinolaryngological treatment method to be used for treatment of sinusitis and the like.

2. Description of Related Art

A paranasal sinus is an intraosseous cavity adjacent to a nasal cavity, and communicates with the nasal cavity through a small hole called the natural ostium. Secretions, bacteria, and the like in the paranasal sinus are excreted into the nasal cavity through the natural ostium. When the mucous membrane in the nasal cavity or paranasal sinus is swollen due to common cold-induced rhinitis or allergic rhinitis or the like, or the inside of the nasal cavity is narrowed due to deflected nasal septum or hypertrophic rhinitis or the like, the natural ostium may become stenosed and chronic inflammation may be generated in the paranasal sinus. Such a disease is called sinusitis. Conventionally, the method for treatment of sinusitis has generally been a surgical operation in which the lesion causing stenosis of the natural ostium is removed by use of forceps and a drill or the like while confirming the video image of the inside of the nasal cavity through an endoscope. In recent years, however, a sinusitis treatment method based on the use of a balloon catheter and not including a surgical operation has been developed, and this method has been drawing attention from the viewpoint of minimal invasiveness to the patient.

In the treatment method developed recently, a guide wire and a balloon catheter are sequentially inserted into the nasal cavity, and, after it is confirmed that the balloon catheter has been disposed in the natural ostium (for example, using a radioscopic method), the balloon catheter is expanded to force open the stenosed part of the natural ostium. According to this treatment method, the communicating passage between the nasal cavity and the paranasal sinus can be recovered without significant bleeding in the nasal cavity or damage to the mucous membrane. In connection with this technique, WO2006/034008 proposes a balloon catheter in which a plurality of radiopaque markers for marking the balloon proximal end, distal end and the like are disposed on the inner surface of the balloon. On the other hand, from the viewpoint of prevention of exposure of the patient to X-rays, there is an increasing demand for a balloon catheter and method of using such which enables easy positioning of the balloon inside the nasal cavity without relying on radioscopy. All documents cited in this disclosure are incorporated herein by reference in their entireties.

SUMMARY

It is an object of the present invention to provide otorhinolaryngological treatment methods in which positioning of an expansion body inside a nasal cavity can be easily carried out without need for radioscopy.

One embodiment of the present invention provides a method for use with a balloon catheter device that includes a selectively bendable portion with a balloon disposed thereon, a control device for controlling bending of the selectively bendable portion, and a camera located at an end of a distal portion, the method comprising inserting the distal portion into the nostril while the distal portion is straight; viewing an image provided by the camera; stopping insertion of the distal portion after the ethmoidal bulla is viewed in the image; articulating the distal portion in an upward direction to view the opening to the frontal sinus ostium or a downward direction to view the opening to the maxillary sinus ostium using the control device; inserting the distal portion into the frontal sinus ostium or the maxillary sinus ostium while the distal portion remains in the bent position; and inflating the balloon in the frontal sinus ostium or the maxillary sinus ostium.

BRIEF DESCRIPTION OF THE DRAWINGS

FIGS. 2A-B show a longitudinal sectional view of a balloon catheter device that can be used in embodiments of the present invention, FIG. 2A showing the device in a non-expanded state, and FIG. 2B showing the device in an expanded state.

FIGS. 4A-B show a longitudinal sectional view of a balloon catheter device that can be used in embodiments of the present invention, FIG. 4A showing the device with a camera and LED light in a non-extended state, and FIG. 4B showing the device with a camera and LED light in an extended state.

FIG. 5A shows the nasal cavity and significant structures therein. FIG. 5B shows the nasal cavity with a balloon catheter positioned in the sphenoidal sinus ostium. FIG. 5N shows removal of the distal end of the balloon catheter from the ostium of the sphenoidal sinus and viewing of the sphenoidal sinus ostium.

FIGS. 6A-R show a method of treating the frontal sinus according to some embodiments of the invention. FIG. 6A shows the nasal cavity and significant structures therein. FIG. 6R shows removal of the distal end of the balloon catheter from the ostium of the frontal sinus and viewing of the frontal sinus ostium.

FIG. 7A shows the nasal cavity and significant structures therein. FIG. 7R shows removal of the distal end of the balloon catheter from the ostium of the maxillary sinus and viewing of the maxillary sinus ostium.

DETAILED DESCRIPTION OF THE PREFERRED EMBODIMENTS

Figure 1:
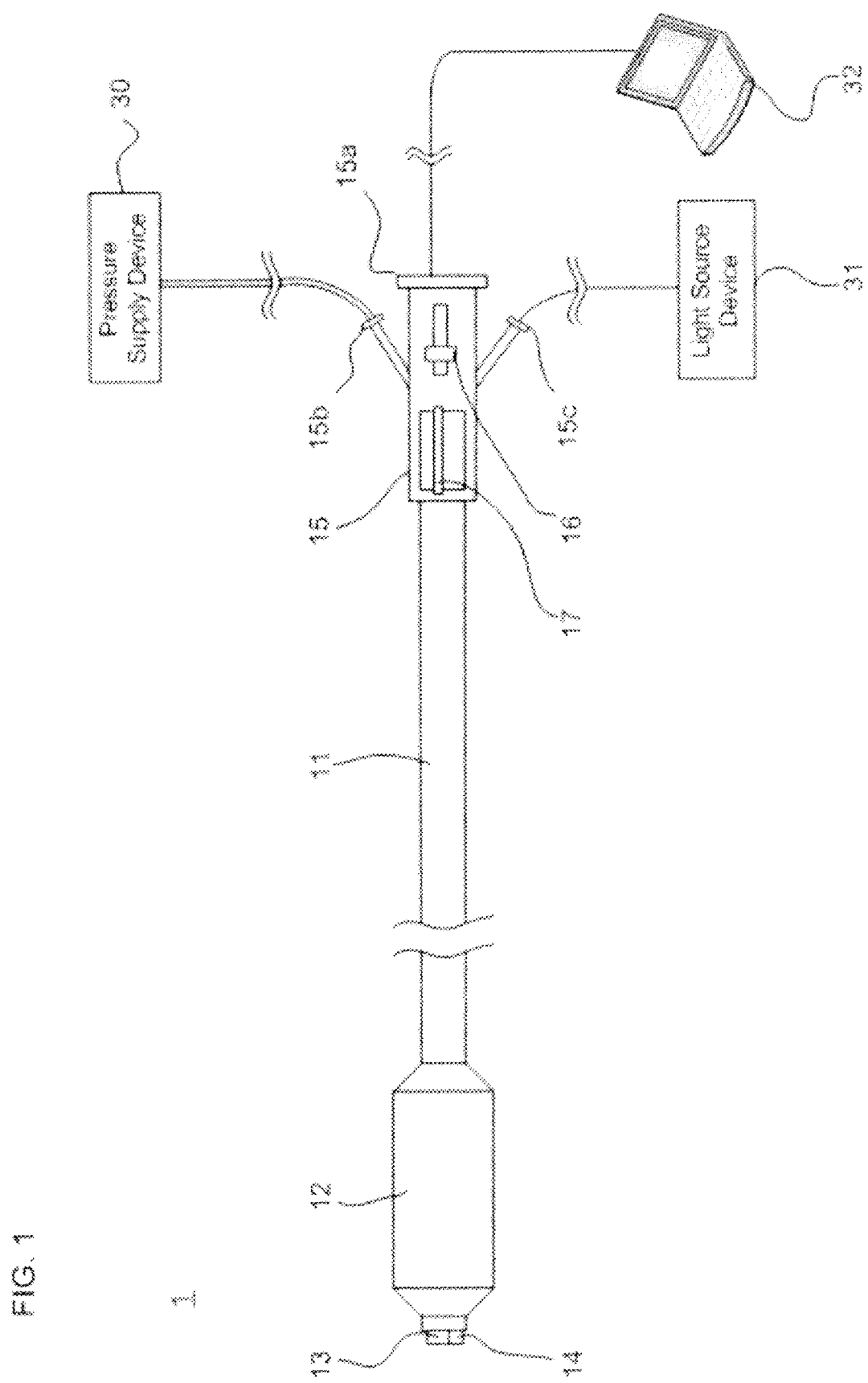
FIG. 1 is a schematic view of a treatment system as used in some embodiments of the present invention.

Embodiments of the present invention are described below referring to the drawings. For convenience of description, the dimensional ratios among components in each of the drawings as well as the dimensional ratios of the same components among the plurality of drawings are modified as required, so that they are not necessarily coincident with the actual ratios.

I. Structure of Treatment Device According to the Present Invention

FIG. 1 is a schematic illustration of the general structure of a treatment system including a catheter 1 as a treatment device according to a first embodiment of the present invention. As shown in FIG. 1, the catheter 1 includes a first elongated body 11 constituting a main body thereof, a balloon 12 as an expansion body for forcing open a stenosed part of a natural ostium, a CCD camera 13 as imaging unit for obtaining an image of the inside of a nasal cavity, an LED light 14 as a lighting unit for illuminating the inside of the nasal cavity, and a hub 15 having the function of a proximal operating section to be operated by the operator as well as the function as a connection port for connection to an external apparatus. Hub 15 has an articulation control 17 and a camera advancement control 16.

Here, the term "CCD camera" means a digital video camera using a CCD image sensor as an imaging element. The hub 15 includes an image port 15a as the connection port for connection to the external apparatus, a pressure supply port 15b, and a light supply port 15c. The ports 15a-15c are described in more detail below. The catheter 1 may be inserted into the patient's nasal cavity from its end portion where the CCD camera 13 is disposed, to be used for treatment of sinusitis. In the following description, the end portion of the catheter 1 for insertion into the nasal cavity will be referred to as distal end, and the end portion on the opposite side will be referred to as proximal end.

As shown in FIG. 1, the balloon catheter 1 is connected to a display device 32 such as an LCD through the image port 15a of the hub 15, to a pressure supply device 30 such as an indeflator through the pressure supply port 15b, and to a light power source device 31 through the light supply port. Here, the display device 32 displays thereon an image obtained by the CCD camera 13. The pressure supply device 30 supplies the balloon 12 with a liquid or the like. The light power source device 31 supplies the LED light 14 with electric power.

The imaging unit in the present embodiment is not restricted to the CCD camera, but may be any of a digital video camera using other imaging element such as a CMOS image sensor, an image fiber for obtaining and transmitting images by means of optical fibers, and an imaging system for transmitting images by means of an objective lens and an optical system including a plurality of relay lenses. The "image obtaining plane" in the cases of using various cameras or optical imaging systems means a predetermined part of the imaging unit disposed so as confront an organ in a living body at the time of introduction into the inside of the living body, and the image obtaining plane may be a distal-end surface of a protective member of the image sensing element or a lens, for example.

The lighting unit in the present embodiment is not limited to the LED light, but may be other lighting units such as a halogen lamp and a high-intensity discharge lamp (HID lamp). Apart from the example shown in FIG. 1 where the LED lamp 14 is attached to the distal end of the catheter 1, the catheter 1 can also be configured such that light generated by the light power source device 31 is guided to its distal end through a light guide made by glass or plastic.

FIGS. 2A and 2B are enlarged illustrations of a longitudinal sectional view showing the vicinity of the distal end of the balloon catheter 1 of FIG. 1. As shown in FIGS. 2A and 2B, the first elongated body 11 has multiple internal lumen. As shown in FIG. 2A, the balloon 12 has a non-expanded state. As shown in FIG. 2B, the balloon 12 has an expanded state.

The change between the non-expanded state and expanded states for balloon 12 as shown in FIGS. 2A and 2B respectively may be effectuated through use of pressure supply device 30 and a lumen of first elongated body 11 in communication with balloon 12 and pressure supply device 30.

Figure 3A:
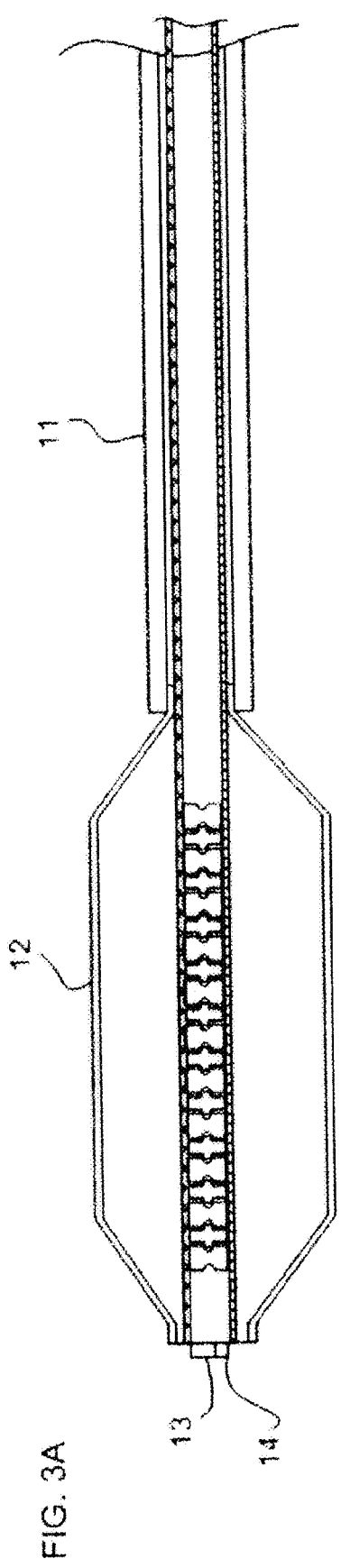
FIGS. 3A-B show a longitudinal sectional view of a balloon catheter device that can be used in embodiments of the present invention, FIG. 3A showing the device in a non-articulated state, and FIG. 3B showing the device in an articulated state.
Figure 3B:
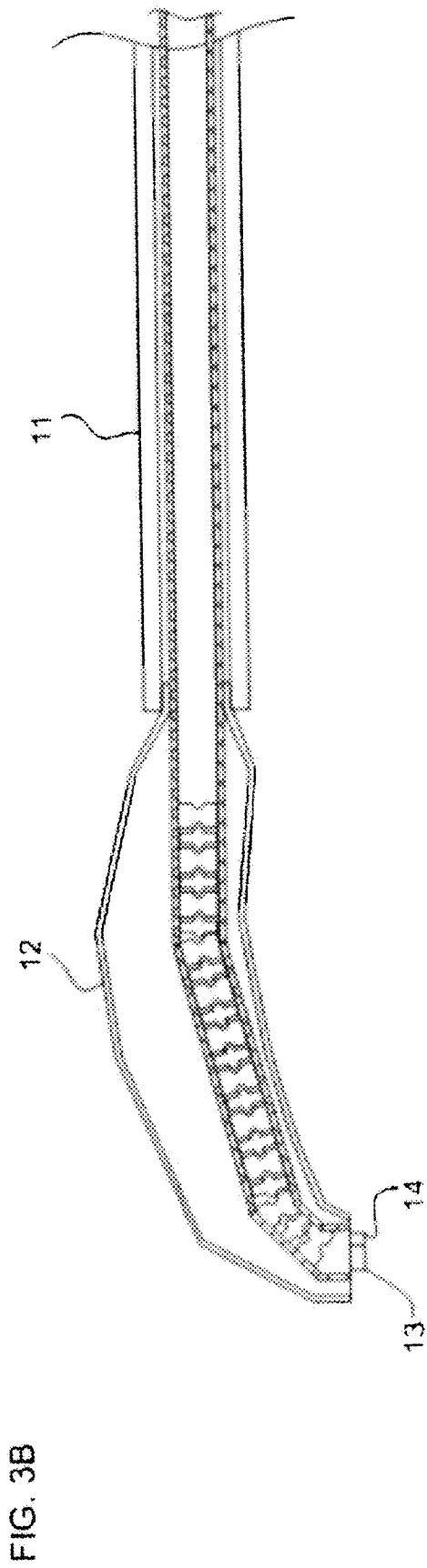

FIGS. 3A and 3B are enlarged illustrations of a longitudinal sectional view showing the vicinity of the distal end of the catheter 1 of FIG. 1. As shown in FIG. 3A, the catheter 1 has a non-articulated state. As shown in FIG. 3B, the catheter 11 has an articulated state. The change between the non-articulated state and articulated states for catheter 1 as shown in FIGS. 3A and 3B respectively is effectuated through use of articulation control 17. Catheter 1 as discussed herein only articulates on a single plane and in a single direction from the non-articulated position shown in FIG. 3A. Changes to this limitation may create slight changes to the methods described herein for other embodiments of the invention. While catheter 1 of FIGS. 3A and 3B may be the same catheter 1 of FIGS. 2A and 2B, the detail of the lumens in the catheter 1 shown in FIGS. 2A and 2B is omitted in FIGS. 3A and 3B for simplicity. The articulation of the catheter device may be performed manually using mechanical articulation devices that are known in the art. The articulation by be performed using electrical devices using, for example, piezoelectric elements or artificial muscle elements. The use of piezoelectric elements is discussed, for example, in U.S. Patent Publication No. 2005/0085693. The articulation may alternatively be performed, for example, using elements made of shape memory alloys that are articulated thermally or electrically. Examples of such devices are described in U.S. Pat. No. 5,624,380 and U.S. Patent Publication No. 2008/0097159.

FIGS. 4A and 4B are enlarged illustrations of a longitudinal sectional view showing the vicinity of the distal end of the catheter 1 of FIG. 1. As shown in FIG. 4A, CCD camera 13 and LED light 14 may have a non-extended state. As shown in FIG. 4B, CCD camera 13 and LED light 14 may have an extended state. The change between the non-extended state and extended states for CCD camera 13 and LED light 14 as shown in FIGS. 4A and 4B respectively is effectuated through use of camera advancement control 16. While catheter 1 of FIGS. 4A and 4B is the same catheter 1 of FIGS. 2A and 2B, the detail of the lumens in the catheter 1 shown in FIGS. 2A and 2B is omitted in FIGS. 4A and 4B for simplicity.

II. Method for Treatment of Sinusitis of the Sphenoidal Sinus

Now, a method of treating sinusitis in the sphenoidal sinus using catheter 1 from FIGS. 1, 2A-B, 3A-B, and 4A-B will be described below referring to FIGS. 5A-N.

Figure 5A:
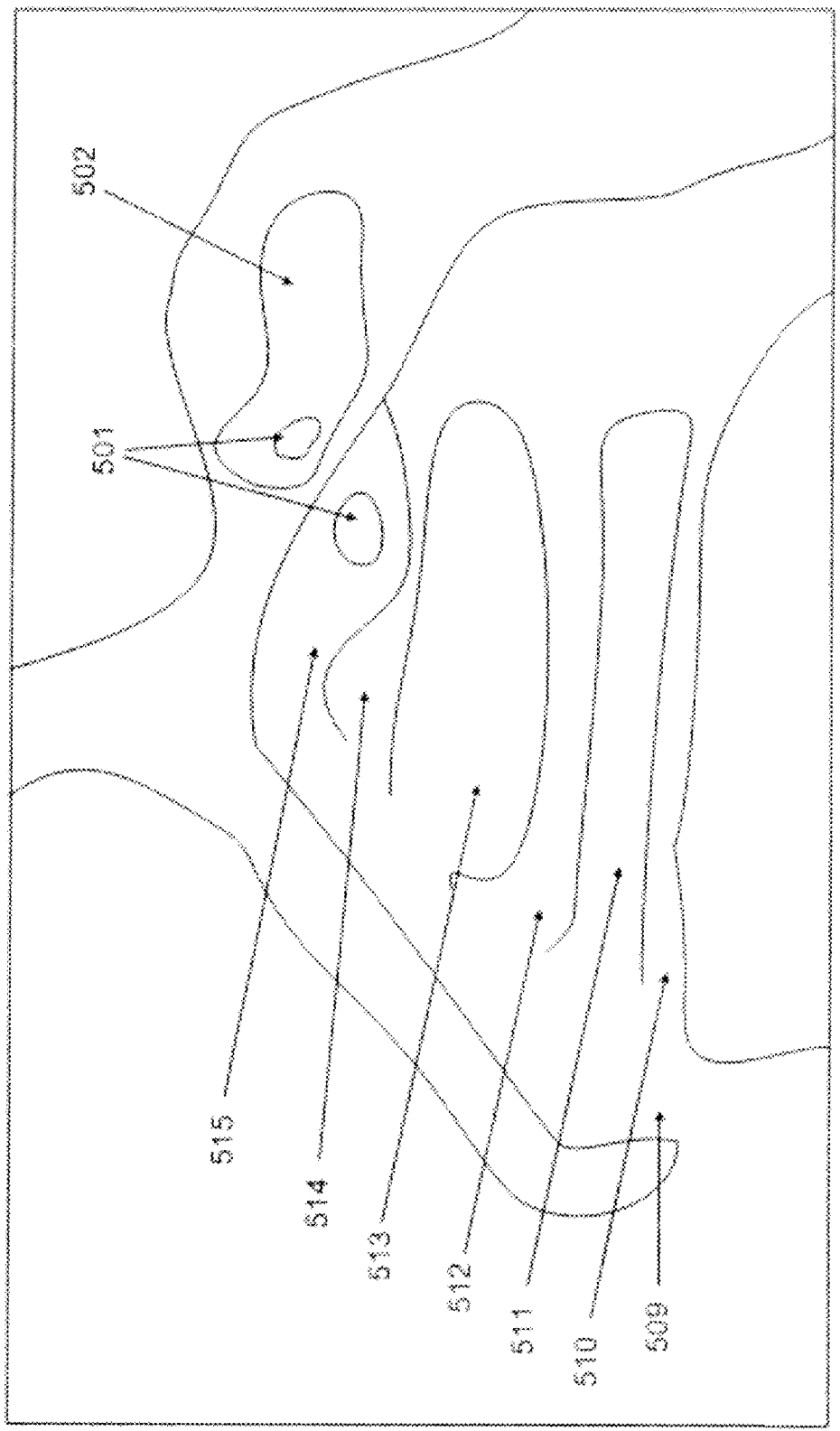
FIGS. 5A-N show a method of treating the sphenoidal sinus according to some embodiments of the invention.

FIG. 5A is an illustration of the nasal cavity and structures therein contained as are pertinent to the present method.

FIG. 5A shows the openings 501 of the sphenoidal sinus that define the ostium connecting sphenoidal sinus 502 to the rest of the nasal cavity. The nasal cavity can be accessed by passing through nasal vestibule 509. Inside the nasal cavity are the inferior nasal turbinate 511, middle nasal turbinate 513, and superior nasal turbinate 515. Defining the spaces between these turbinates are inferior nasal meatus 510, middle nasal meatus 512, and superior nasal meatus 514. FIG. 5B shows the same structures of FIG. 5A with catheter 1 having elongated body 11 and balloon 12 properly positioned for treating sinusitis of sphenoidal sinus 502. The following discussion explains how the positioning shown in FIG. 5B is achieved.

Figure 5C:
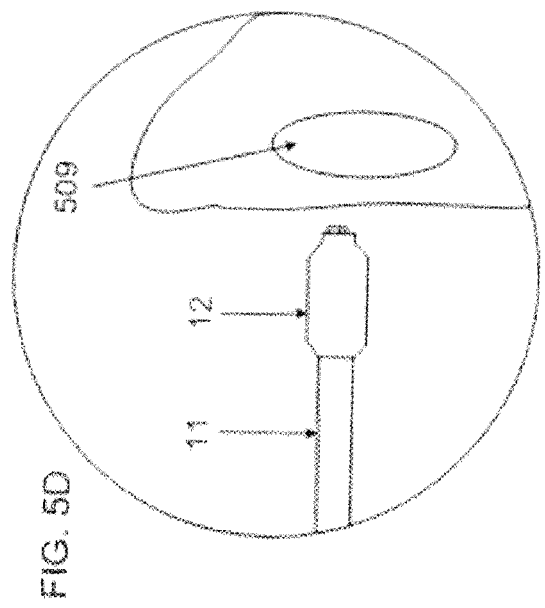
FIG. 5C shows the positioning of the balloon catheter for downward articulation.
Figure 5D:
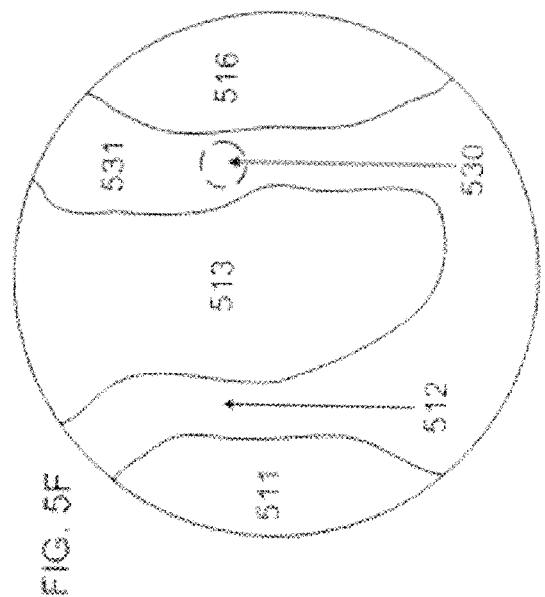
FIG. 5D shows approach of the distal end of the balloon catheter to the nasal cavity.
Figure 5E:
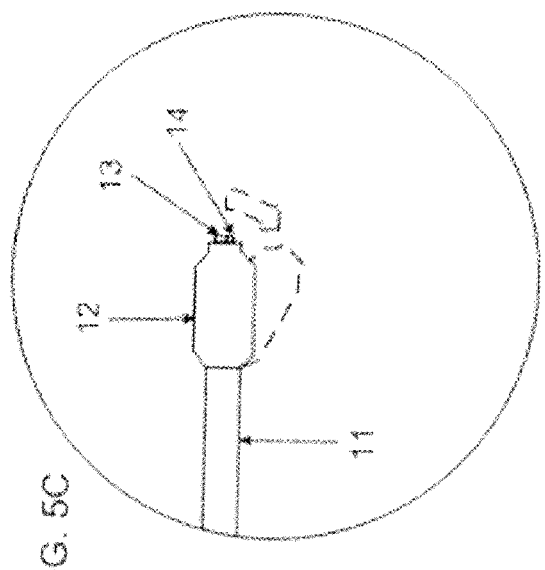
FIG. 5E shows insertion of the distal end of the balloon catheter into the nasal cavity.

As shown in FIG. 5C, catheter 1 is first positioned so it will articulate in a downwards direction from its non-articulated position. With catheter 1 properly positioned for downward articulation, the catheter distal end is positioned to enter the nasal cavity through nasal vestibule 509 as shown in FIG. 5D. As shown in FIG. 5E, the catheter 1 is advanced into the nasal cavity through nasal vestibule 509 so that balloon 12, CCD camera 13, and LED light 14 fully enter the nasal cavity.

Figure 5F:
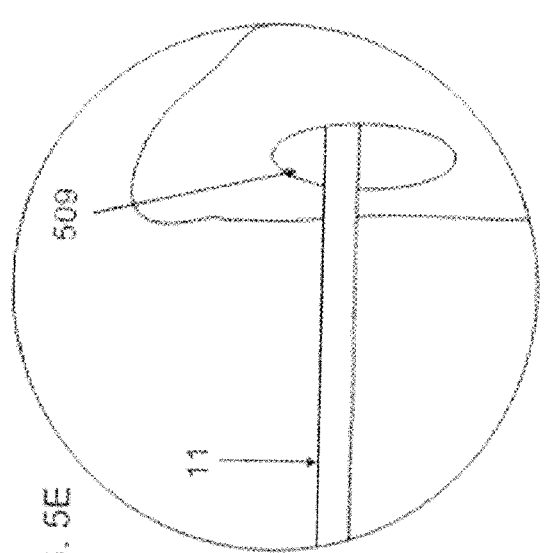
FIG. 5F shows advancing the distal end of the balloon catheter to the side of the middle turbinate.

FIG. 5F is an illustration of a view of the inside of the nasal cavity as seen using CCD camera 13. As shown, the operator of the catheter 1 identifies middle nasal turbinate 513 and nasal septum 516. Inferior nasal turbinate 511 and middle nasal meatus 512 are shown and labeled for clarity. Having identified middle nasal turbinate 513 and nasal septum 516, the operator advances the distal end of catheter 1 between those two structures through the common nasal meatus 531 in an area roughly identified as area 530. FIG. 5G is an image as seen through a CCD camera 13 while performing the movement as described with reference to FIG. 5F.

Figure 5H:
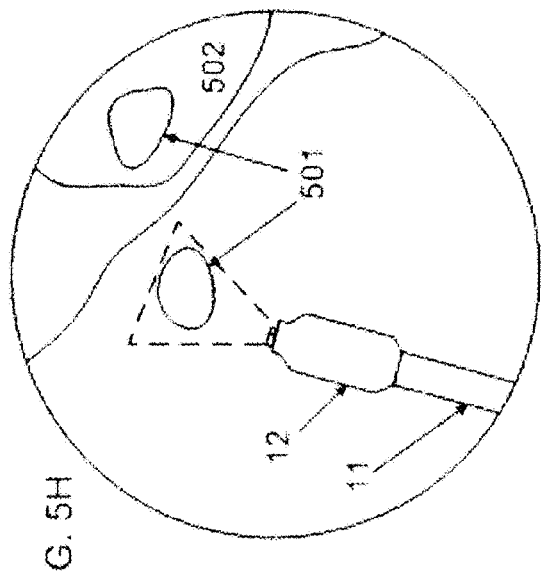
FIG. 5H shows approach of the distal end of the balloon catheter to one of the openings to the ostium of the sphenoidal sinus.
Figure 5J:
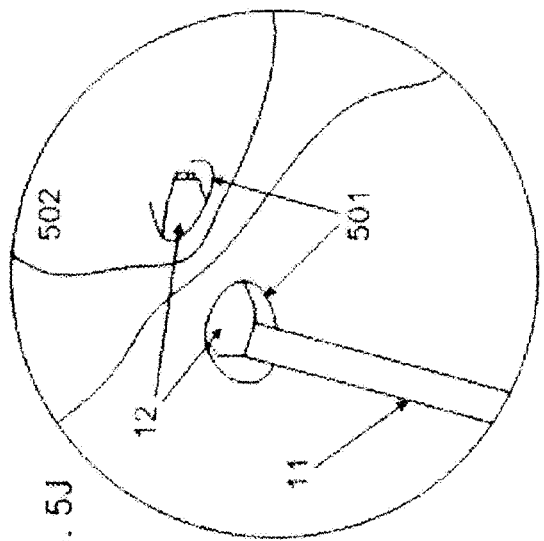
FIG. 5J shows insertion of the distal end of the balloon catheter into the ostium of the sphenoidal sinus.
Figure 5G:
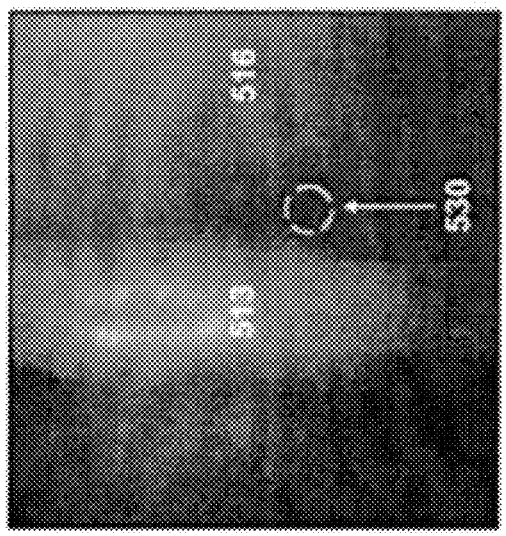
FIG. 5G shows an image roughly corresponding to FIG. 5F as seen through a CCD camera.
Figure 5I:
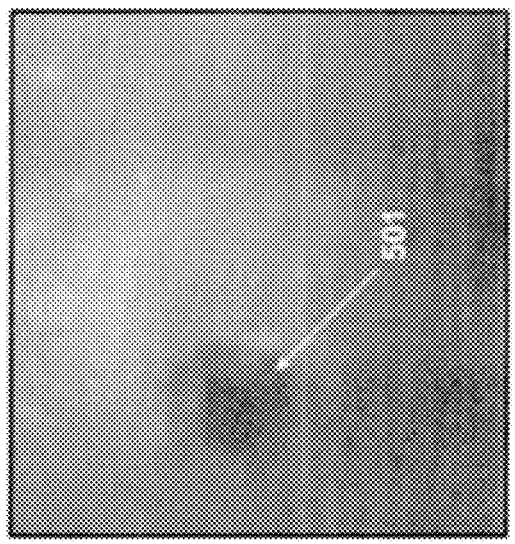
FIG. 5I shows an image roughly corresponding to FIG. 5H as seen through a CCD camera.
Figure 5L:
FIG. 5L shows an image roughly corresponding to FIG. 5J as seen through a CCD camera.

Having advanced catheter 1 through area 530, the operator uses CCD camera 13 to advance the distal end of catheter 1 until the opening 501 of the sphenoidal sinus 502 is visible as shown in FIG. 5H. FIG. 5I is an image as seen through a CCD camera 13 while performing the movement as described with reference to FIG. 5H. Where other openings, other than the desired opening 501 exist in the same general area as opening 501, the operator may need to observe the openings using the CCD camera 13 as shown in FIG. 5I1 and FIG. 5I in order to identify the correct ostium for insertion. Continuing to advance the distal end of catheter 1 toward the opening 501 of sphenoidal sinus 502, the operator advances the balloon 12 into the sphenoidal sinus ostium, which connects the sphenoidal sinus 502 to the rest of the nasal cavity as shown in FIG. 5J. As depicted, the operator may need to articulate the distal end of catheter 1 as the distal end is advanced through the ostium so that the catheter 1 will continue advancing along the path of that ostium. FIG. 5K is an image as seen through a CCD camera 13 while performing the movement as described with reference to FIG. 5J. In particular, FIG. 5K shows the inside of the sphenoidal sinus ostium and the opening 501 of the sphenoidal sinus 502 that exits the sphenoidal sinus ostium and enters the sphenoidal sinus 502. As such, the image shows how the operator may view the opening 501 of the sphenoidal sinus 502 as he advances the distal end of catheter 1 through the sphenoidal sinus ostium. FIG. 5L is an image as seen through a CCD camera 13 while performing the movement as described with reference to FIG. 5J, wherein the distal end of catheter 1 has been advanced through the sphenoidal sinus ostium and now is sufficiently advanced into the sphenoidal sinus 502 so as to allow the operator to view the interior wall of the sphenoidal sinus 502 In some situations, it may be advantageous to advance the distal end of catheter 1 until it just enters the sphenoidal sinus 502, and then use the camera advancement control 16 to advance just the CCD camera 13 and LED light 14 further into the sphenoidal sinus 502 in order to see the interior wall of the sphenoidal sinus 502 as shown in FIG. 5L.

Figure 5N:
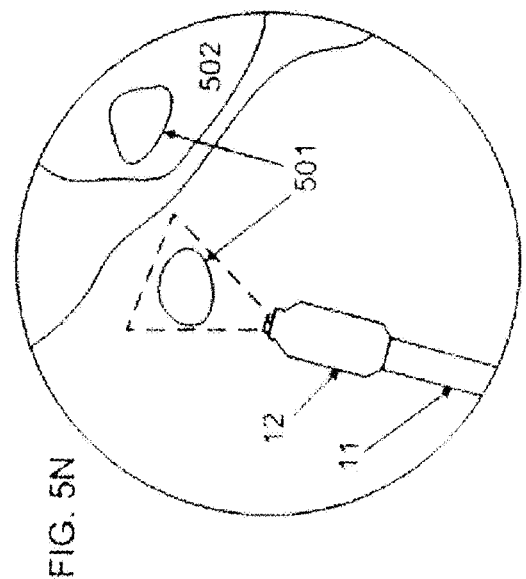
Figure 5K:
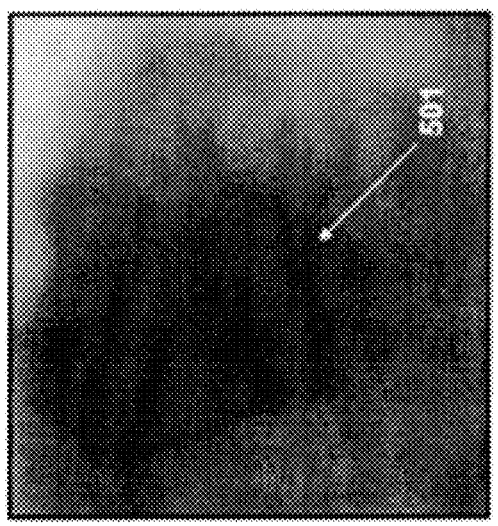
FIG. 5K shows an image roughly corresponding to FIG. 5J as seen through a CCD camera.
Figure 5M:
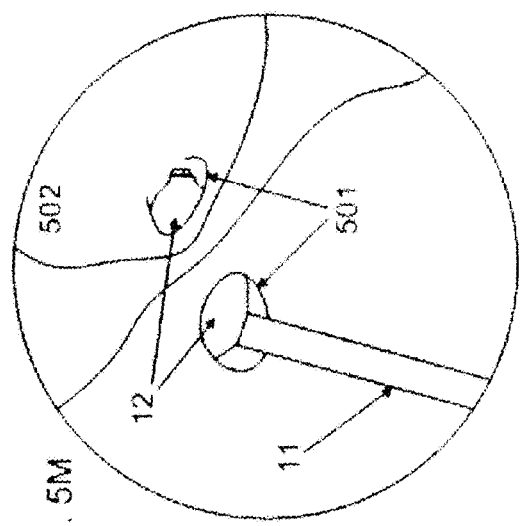
FIG. 5M shows expansion of the balloon catheter.

Once balloon 12 is positioned in the sphenoidal sinus ostium, the operator changes balloon 12 to its expanded state as shown in FIG. 5M. This expansion is effective to correct the stenosis of the ostium. Once treatment by means of expansion is complete, the operator returns balloon 12 to its non-expanded state and removes it from the ostium. This removal may require articulation of the distal end of catheter 12 substantially in reverse of the articulation that the operator effectuated to allow the balloon 12 to enter the ostium.

Once the balloon 12 is fully removed from the ostium, the operator can use CCD camera 13 to inspect the ostium in order to verify that the treatment was successful to correct the stenosis of the ostium as shown in FIG. 5N. The operator then removes catheter 1 from the nasal cavity.

III. Method for Treatment of Sinusitis of the Frontal Sinus

A method of treating sinusitis in the frontal sinus using balloon catheter 1 will be described below referring to FIGS. 6A-R.

FIG. 6A is an illustration of the nasal cavity and structures therein contained as are pertinent to the present method.

FIG. 6A shows the openings 601 of the frontal sinus 602 that define the ostium connecting frontal sinus 602 to the rest of the nasal cavity. The lower opening 601 of the frontal sinus 602 is shown in broken line to indicate that it is obscured behind tissue of the nasal cavity and as such is not directly visible in the present view of the nasal cavity. FIG. 6A shows the structures present in FIG. 5A, including: nasal vestibule 509, inferior nasal turbinate 511, middle nasal turbinate 513, superior nasal turbinate 515, inferior nasal meatus 510, middle nasal meatus 512, and superior nasal meatus 514. Middle nasal turbinate 513 is filled with a slanted line pattern to indicate that part of the structure has been cut away in this illustration to allow the viewing of other structures that would otherwise be obscured. FIG. 6A additionally shows ethmoidal bulla 610, uncinate process 611, and a groove 612 between the ethmoidal bulla 610 and uncinate process 611.

Figure 6B:
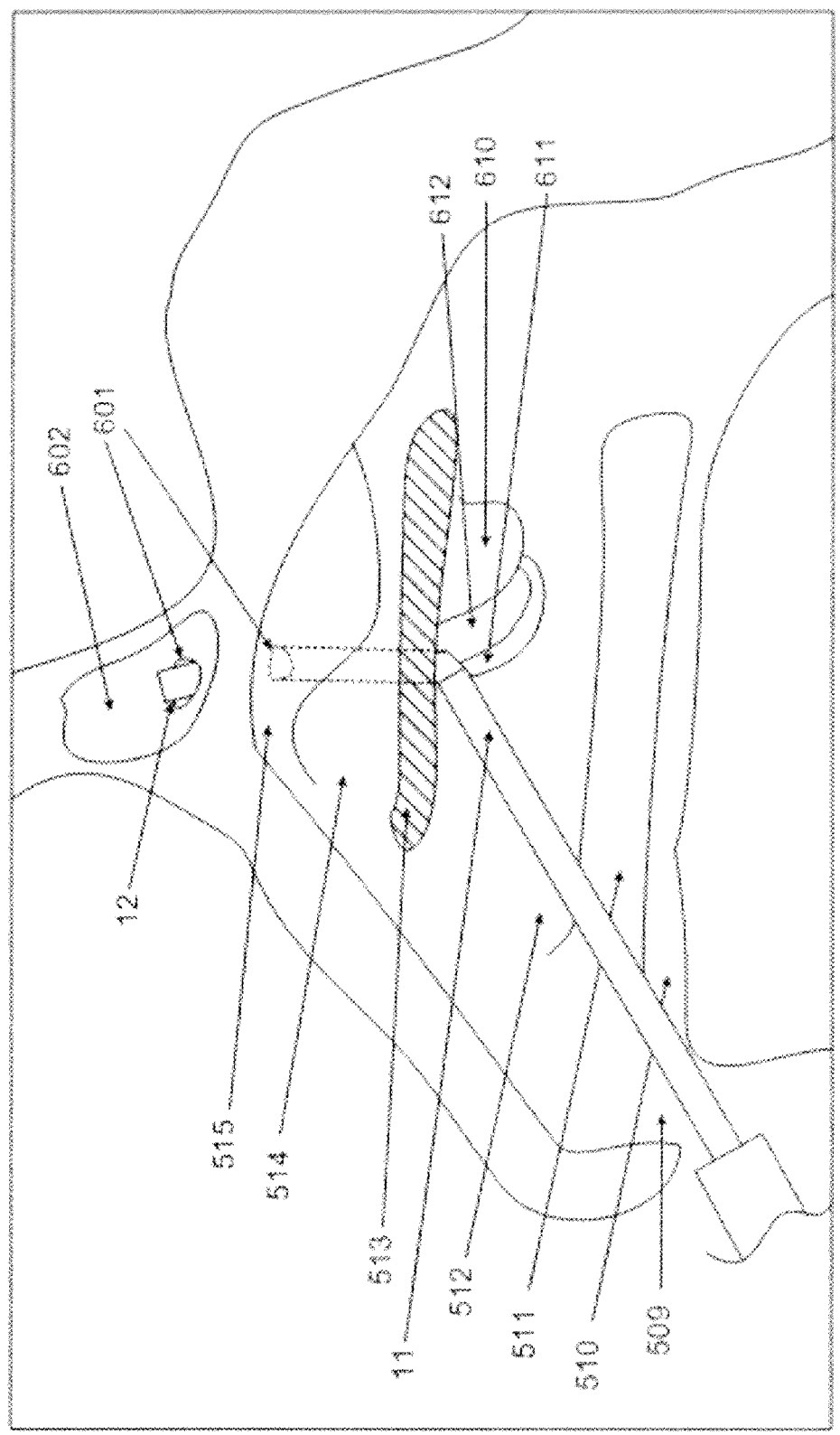
FIG. 6B shows the nasal cavity with a balloon catheter positioned in the frontal sinus ostium.

FIG. 6B shows the same structures of FIG. 6A with catheter 1 having elongated body 11 and balloon 12 properly positioned for treating sinusitis of frontal sinus 602. The following discussion explains how the positioning shown in FIG. 6B is achieved.

Figure 6C:
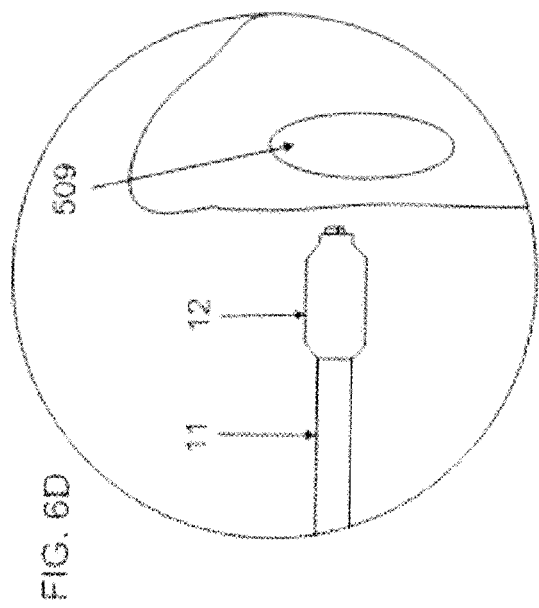
FIG. 6C shows the positioning of the balloon catheter for upward articulation.
Figure 6D:
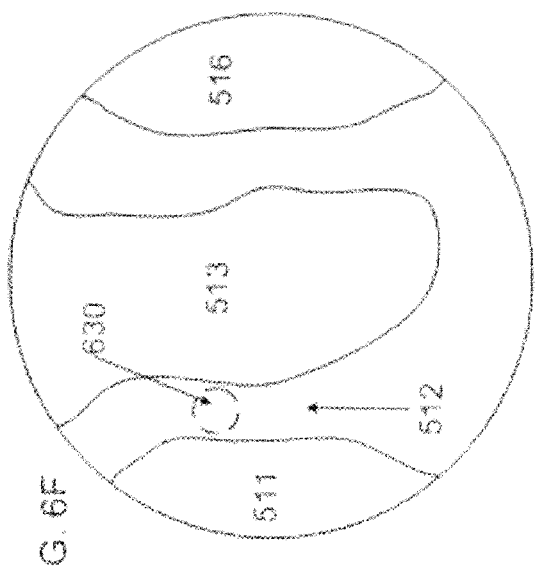
FIG. 6D shows approach of the distal end of the balloon catheter to the nasal cavity.
Figure 6E:
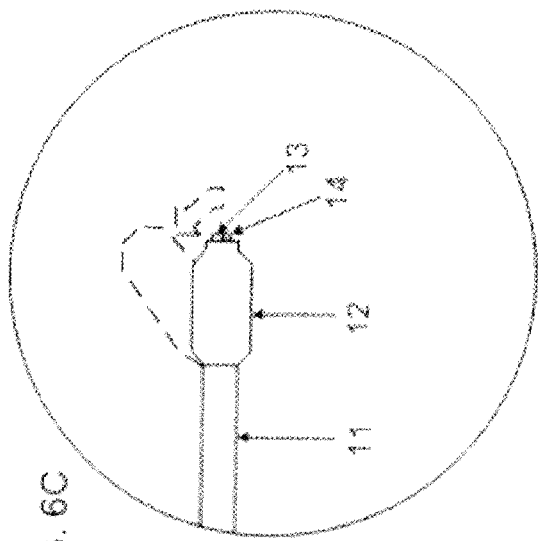
FIG. 6E shows insertion of the distal end of the balloon catheter into the nasal cavity.

As shown in FIG. 6C, catheter 1 is first positioned so it will articulate in an upwards direction from its non-articulated position. With catheter 1 properly positioned for upward articulation, the catheter distal end is positioned to enter the nasal cavity through nasal vestibule 509 as shown in FIG. 6D. As shown in FIG. 6E, the catheter 1 is advanced into the nasal cavity through nasal vestibule 509 so that balloon 12, CCD camera 13, and LED light 14 fully enter the nasal cavity.

Figure 6F:
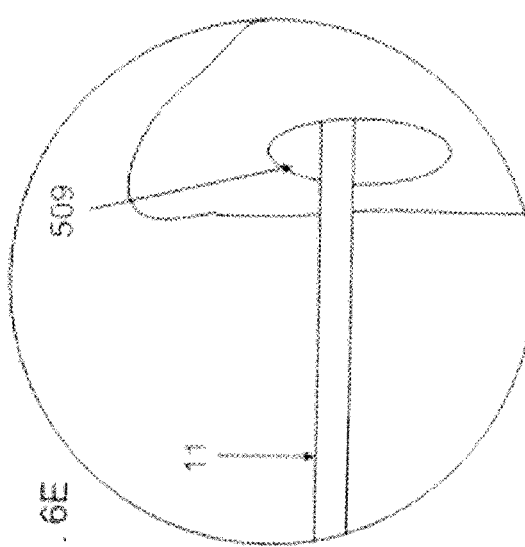
FIG. 6F shows advancing the distal end of the balloon catheter to the side of the middle turbinate.

FIG. 6F is an illustration of a view of the inside of the nasal cavity as seen using CCD camera 13. As shown, the operator of the catheter 1 identifies middle nasal turbinate 513 and nasal septum 516. Inferior nasal turbinate 511 and middle nasal meatus 512 are shown and labeled for clarity. Having identified middle nasal turbinate 513 and nasal septum 516, the operator advances the distal end of catheter 1 in the space at the side of middle nasal meatus 512 that is opposite of nasal septum 516 as identified as area 630. FIG. 6G is an image as seen through a CCD camera 13 while performing the movement as described with reference to FIG. 6F.

Figure 6H:
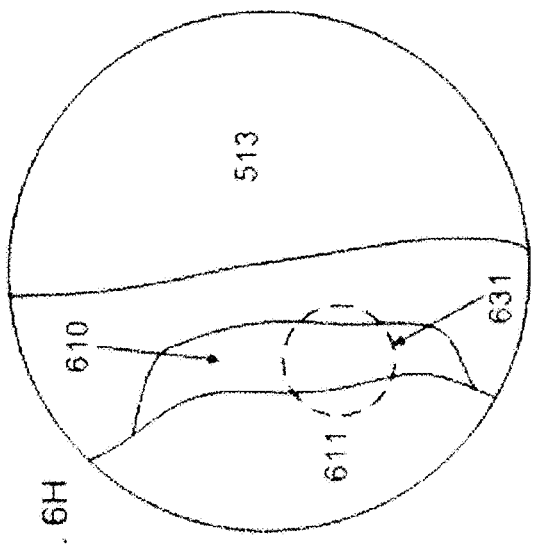
FIG. 6H shows approach of the distal end of the balloon catheter to the ethmoidal bulla.

Having advanced catheter 1 through area 630, the operator uses CCD camera 13 to advance the distal end of catheter 1 until the ethmoidal bulla 610 is in view as shown in FIG. 6H. The operator advances the distal end of catheter 1 past the uncinate process 611 and approaches the ethmoidal bulla 610 until nearly touching it. This movement entails moving towards the area 631. FIG. 6I is an image as seen through a CCD camera 13 while performing the movement as described with reference to FIG. 6H.

Figure 6J:
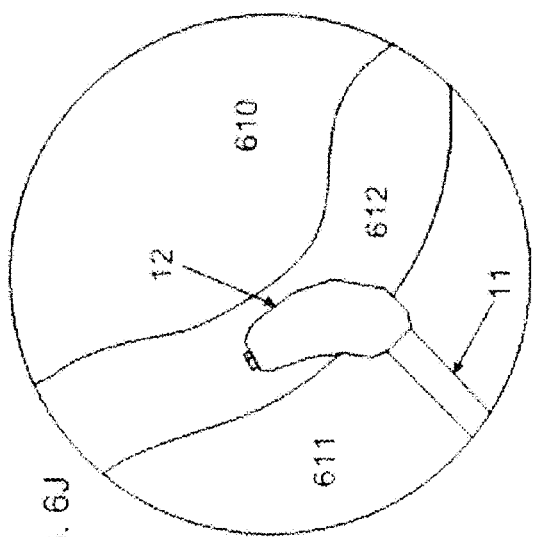
FIG. 6J shows advancing the distal end of the balloon catheter along the groove (hiatus semilunaris) between the ethmoidal bulla and the uncinate process.
Figure 6G:
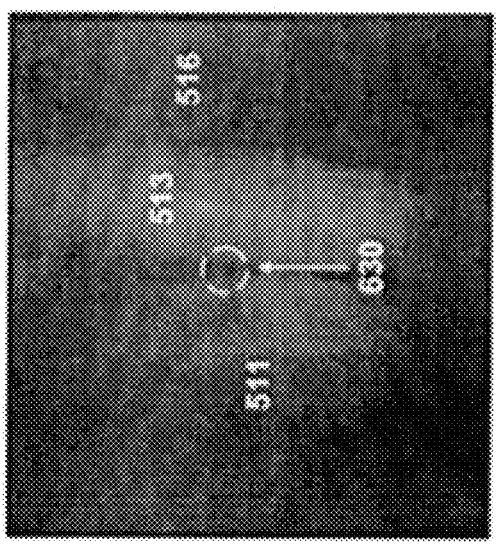
FIG. 6G shows an image roughly corresponding to FIG. 6F as seen through a CCD camera.
Figure 6I:
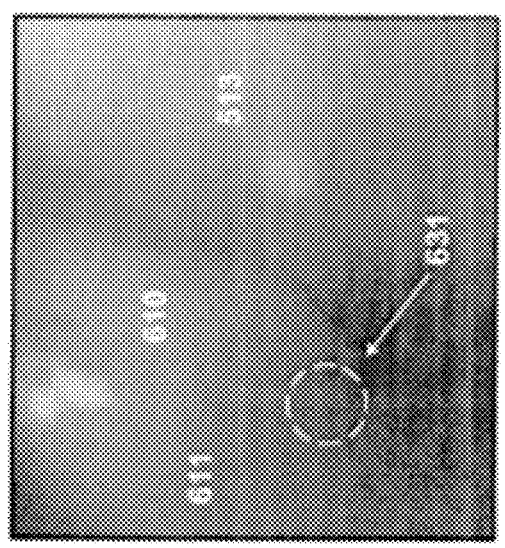
FIG. 6I shows an image roughly corresponding to FIG. 6H as seen through a CCD camera.

Once the operator has advanced the distal end of catheter 1 sufficiently close to the ethmoidal bulla 610, the operator articulates the distal end of the catheter 1 in an upward direction and is then able to view the groove 612 between ethmoidal bulla 610 and uncinate process 611 as shown in FIG. 6J. The operator advances the distal end of catheter 1 in this upward articulated state along groove 612 as also shown in FIG. 6J. FIG. 6K is an image as seen through a CCD camera 13 while performing the movement as described with reference to FIG. 6J.

Figure 6L:
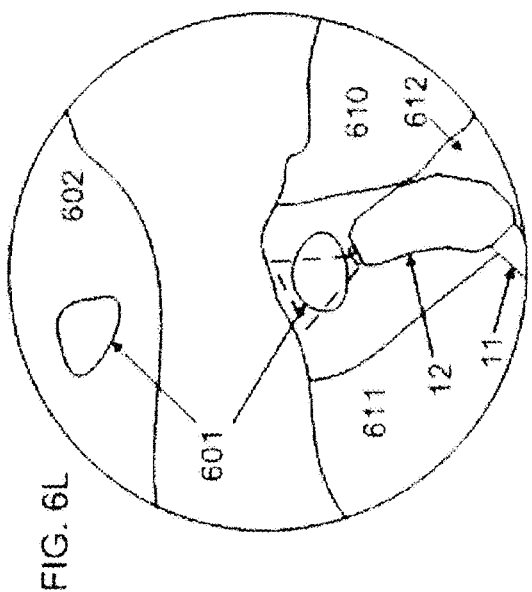
FIG. 6L shows approach of the distal end of the balloon catheter to one of the openings to the ostium of the frontal sinus.
Figure 6N:
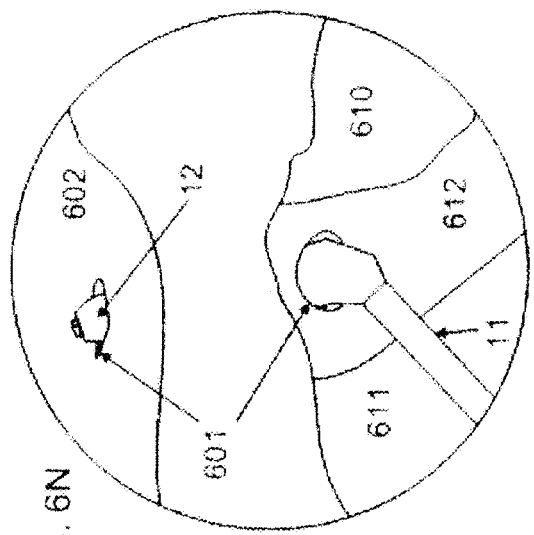
FIG. 6N shows insertion of the distal end of the balloon catheter into the ostium of the frontal sinus.
Figure 6K:
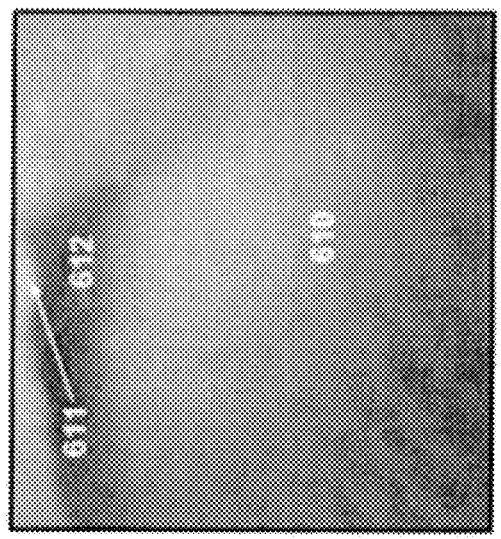
FIG. 6K shows an image roughly corresponding to FIG. 6J as seen through a CCD camera.
Figure 6M:
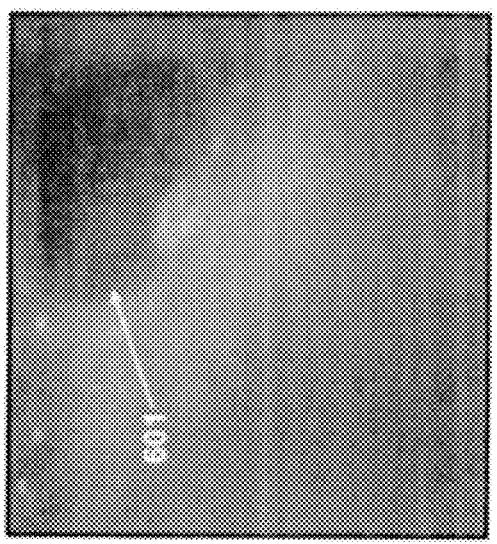
FIG. 6M shows an image roughly corresponding to FIG. 6L as seen through a CCD camera.
Figure 6P:
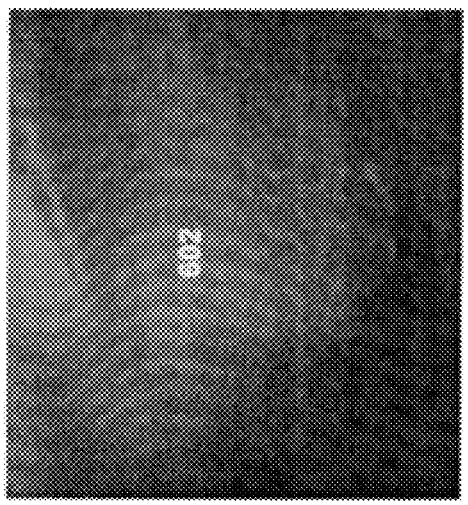
FIG. 6P shows an image roughly corresponding to FIG. 6N as seen through a CCD camera.

The operator advances the distal end of catheter 1 along groove 612 until the opening 601 of the frontal sinus 602 is visible as shown in FIG. 6L. FIG. 6M is an image as seen through a CCD camera 13 while performing the movement as described with reference to FIG. 6L. Where other openings, other than the desired opening 601 exist in the same general area as opening 601, the operator may need to observe the openings using the CCD camera 13 as shown in FIG. 6L and FIG. 6M in order to identify the correct ostium for insertion. Continuing to advance the distal end of catheter 1 toward the opening 601 of frontal sinus 602, the operator advances the balloon 12 into the ostium connecting frontal sinus 602 to the rest of the nasal cavity as shown in FIG. 6N. As depicted, the operator may need to articulate the distal end of catheter 1 as that distal end is advanced through the ostium so that the catheter 1 will continue advancing along the path of that ostium. FIG. 6O is an image as seen through a CCD camera 13 while performing the movement as described with reference to FIG. 6N. In particular, FIG. 6O shows the inside of the frontal sinus ostium and the opening 601 of the frontal sinus 602 that exits the frontal sinus ostium and enters the frontal sinus 602. As such, the image shows how the operator may view the opening 601 of the frontal sinus 602 as he advances the distal end of catheter 1 through the frontal sinus ostium. FIG. 6P is an image as seen through a CCD camera 13 while performing the movement as described with reference to FIG. 6N, wherein the distal end of catheter 1 has been advanced through the frontal sinus ostium and now is sufficiently advanced into the frontal sinus 602 so as to allow the operator to view the interior wall of the frontal sinus 602. In some situations, it may be advantageous to advance the distal end of catheter 1 until it just enters the frontal sinus 602, and then use the camera advancement control 16 to advance just the CCD camera 13 and LED light 14 further into the frontal sinus 602 in order to see the interior wall of the frontal sinus 602 as shown in FIG. 6P. In some situations, it may be necessary to expand the balloon 12 to correct stenosis of the passages leading to the openings 601 of the frontal sinus 602.

Figure 6R:
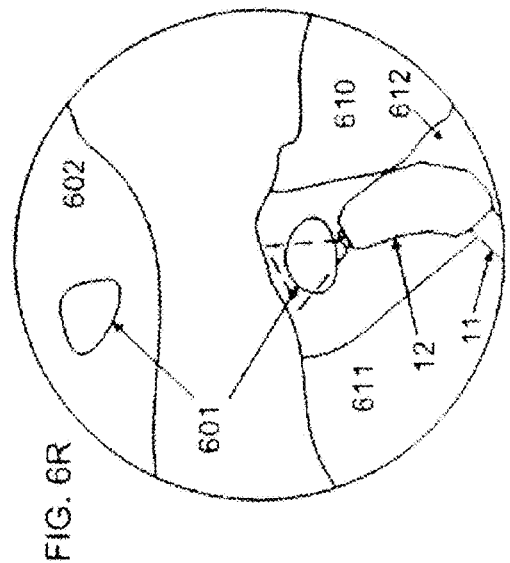
Figure 6O:
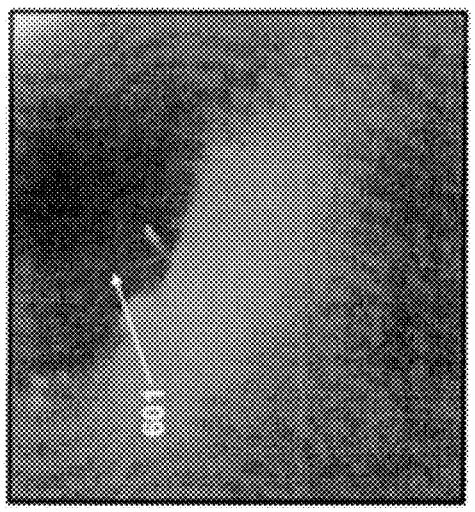
FIG. 6O shows an image roughly corresponding to FIG. 6N as seen through a CCD camera.
Figure 6Q:
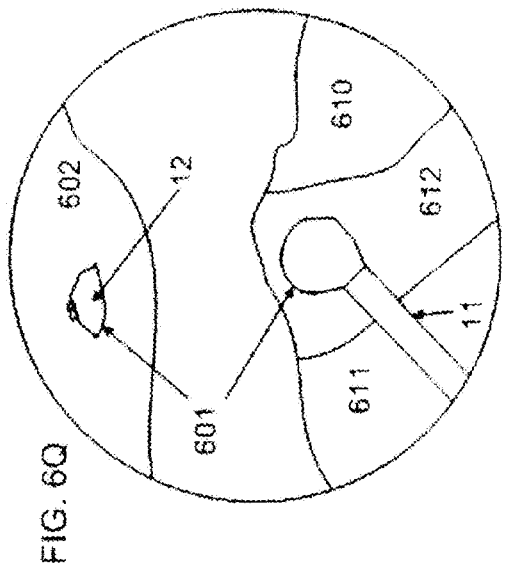
FIG. 6Q shows expansion of the balloon catheter.

Once balloon 12 is positioned between openings 601 of the frontal sinus 602, the operator changes balloon 12 to its expanded state as shown in FIG. 6Q. This expansion is effective to correct the stenosis of the ostium. Once treatment by means of expansion is complete, the operator returns balloon 12 to its non-expanded state and removes it from the ostium. This removal may require articulation of the distal end of catheter 12 substantially in reverse of the articulation that the operator effectuated to allow the balloon 12 to enter the ostium.

Once the balloon 12 is fully removed from the ostium, the operator can use CCD camera 13 to inspect the ostium in order to verify that the treatment was successful to correct the stenosis of the ostium as shown in FIG. 6R. The operator then removes catheter 1 from the nasal cavity.

IV. Method for Treatment of Sinusitis of the Maxillary Sinus

Now, a method of treating sinusitis in the maxillary sinus using catheter 1 from FIGS. 1, 2A-B, 3A-B, and 4A-B will be described below referring to FIGS. 7A-R.

Figure 7A:
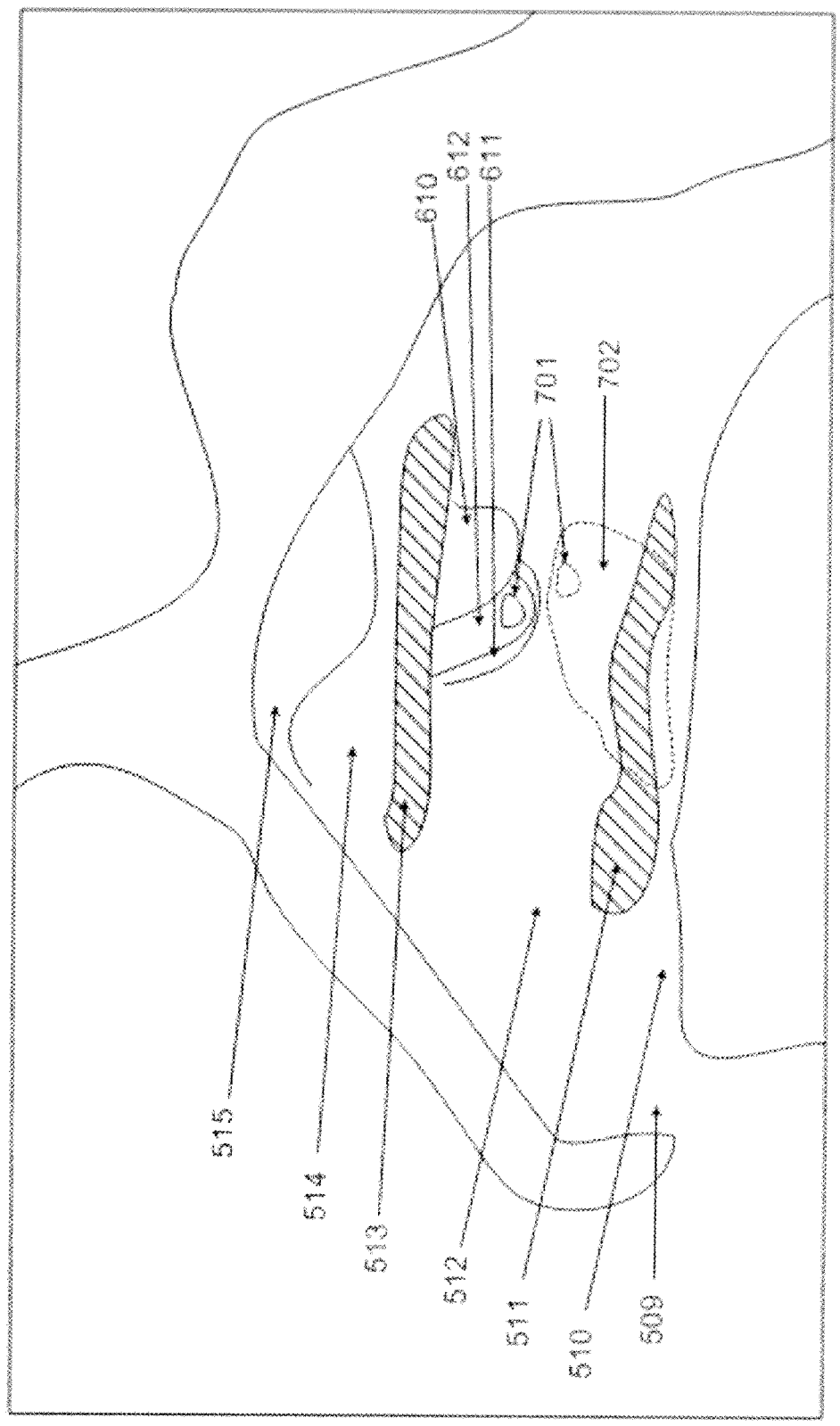
FIGS. 7A-R show a method of treating the maxillary sinus according to some embodiments of the invention.

FIG. 7A is an illustration of the nasal cavity and structures therein contained as are pertinent to the present method.

FIG. 7A shows the openings 701 of the maxillary sinus 702 that define the ostium connecting maxillary sinus 702 to the rest of the nasal cavity. The lower opening 701 of the maxillary sinus 702 is shown in broken line to indicate that it is obscured behind tissue of the nasal cavity and as such is not directly visible in the present view of the nasal cavity. The maxillary sinus 702 is likewise shown in broken line as it would be obscured by tissue as being in the background of the present view of the nasal cavity. FIG. 7A shows the structures present in FIG. 6A, including: nasal vestibule 509, inferior nasal turbinate 511, middle nasal turbinate 513, superior nasal turbinate 515, inferior nasal meatus 510, middle nasal meatus 512, superior nasal meatus 514, ethmoidal bulla 610, uncinate process 611, and a groove 612 between the ethmoidal bulla 610 and uncinate process 611. Superior nasal turbinate 515, middle nasal turbinate 513, and inferior nasal turbinate 511 are filled with a slanted line pattern to indicate that part of each of these structures has been cut away in this illustration to allow the viewing of other structures that would otherwise be obscured.

Figure 7B:
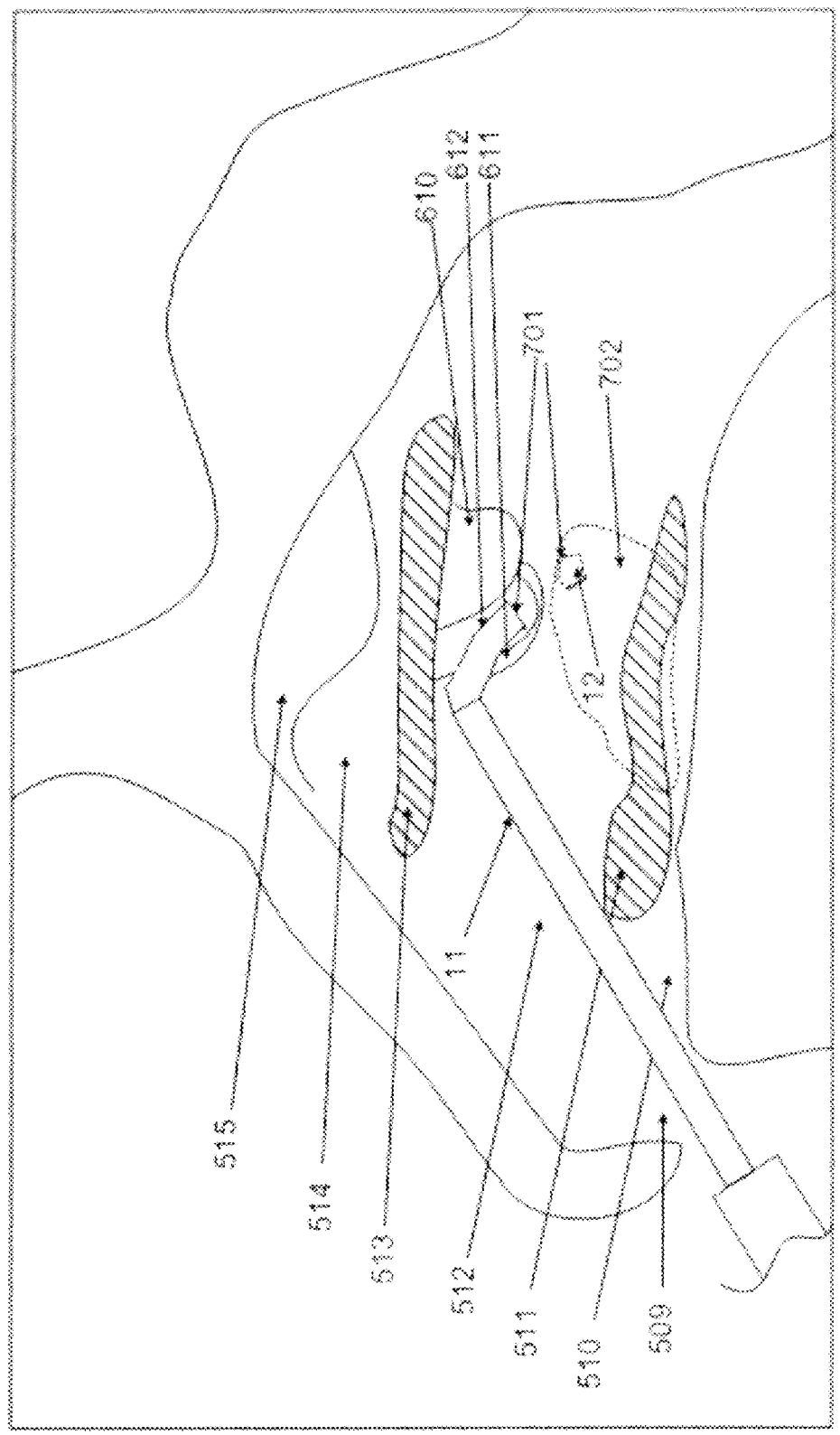
FIG. 7B shows the nasal cavity with a balloon catheter positioned in the maxillary sinus ostium.

FIG. 7B shows the same structures of FIG. 7A with catheter 1 having elongated body 11 and balloon 12 properly positioned for treating sinusitis of maxillary sinus 702. The following discussion explains how the positioning shown in FIG. 7B is achieved.

Figure 7C:
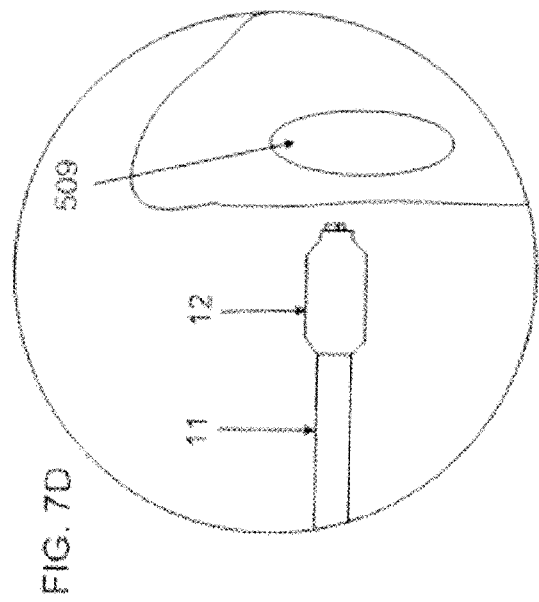
FIG. 7C shows the positioning of the balloon catheter for downward articulation.
Figure 7D:
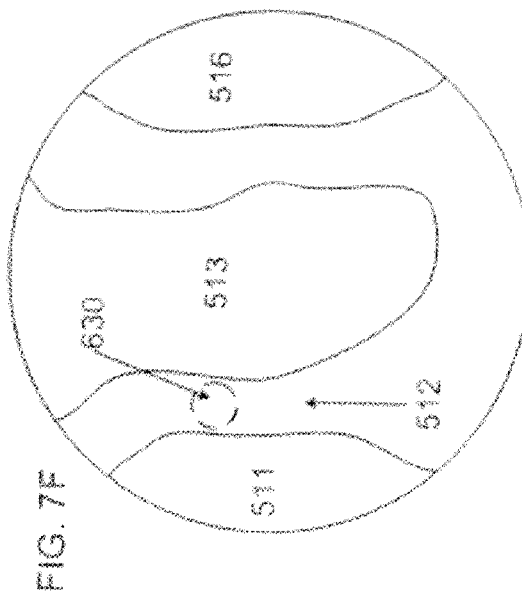
FIG. 7D shows approach of the distal end of the balloon catheter to the nasal cavity.
Figure 7E:
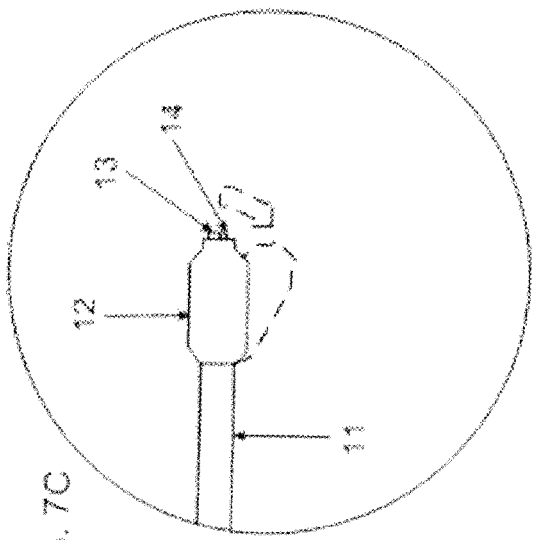
FIG. 7E shows insertion of the distal end of the balloon catheter into the nasal cavity.

As shown in FIG. 7C, catheter 1 is first positioned so it will articulate in a downwards direction from its non-articulated position. With catheter 1 properly positioned for downward articulation, the catheter distal end is positioned to enter the nasal cavity through nasal vestibule 509 as shown in FIG. 7D. As shown in FIG. 7E, the catheter 1 is advanced into the nasal cavity through nasal vestibule 509 so that balloon 12, CCD camera 13, and LED light 14 fully enter the nasal cavity.

Figure 7F:
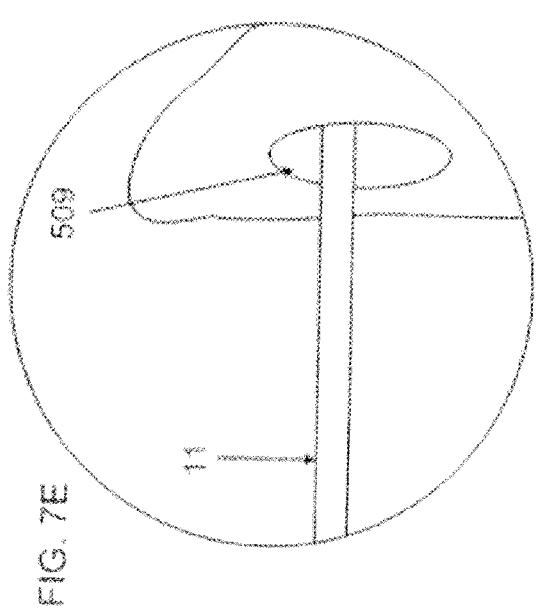
FIG. 7F shows advancing the distal end of the balloon catheter to the side of the middle turbinate.

FIG. 7F is an illustration of a view of the inside of the nasal cavity as seen using CCD camera 13. As shown, the operator of the catheter 1 identifies middle nasal turbinate 513 and nasal septum 516. Inferior nasal turbinate 511 and middle nasal meatus 512 are shown and labeled for clarity. Having identified middle nasal turbinate 513 and nasal septum 516, the operator advances the distal end of catheter 1 in the space at the side of middle nasal meatus 512 that is opposite of nasal septum 516 as identified as area 630. FIG. 7G is an image as seen through a CCD camera 13 while performing the movement as described with reference to FIG. 7F.

Figure 7H:
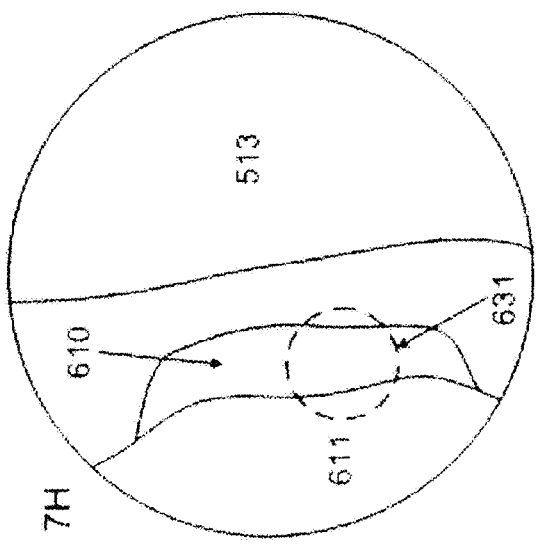
FIG. 7H shows approach of the distal end of the balloon catheter to the ethmoidal bulla.

Having advanced catheter 1 through area 630, the operator uses CCD camera 13 to advance the distal end of catheter 1 until the ethmoidal bulla 610 is in view as shown in FIG. 7H. The operator advances the distal end of catheter 1 past the uncinate process 611 and approaches the ethmoidal bulla 610 until nearly touching it. This movement entails moving towards the area 631. FIG. 7I is an image as seen through a CCD camera 13 while performing the movement as described with reference to FIG. 7H.

Figure 7J:
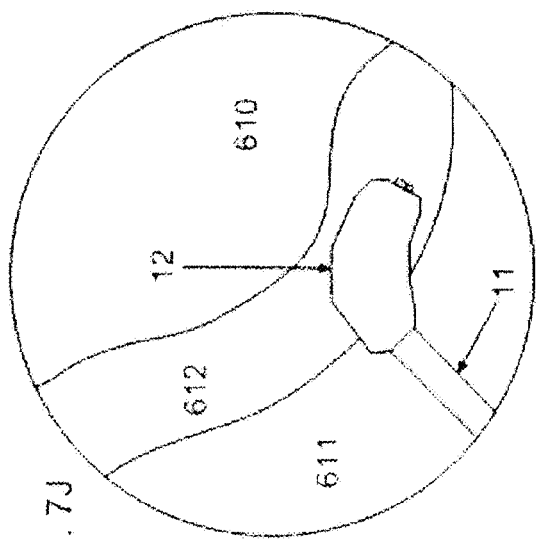
FIG. 7J shows advancing the distal end of the balloon catheter along the groove between the ethmoidal bulla and the uncinate process.
Figure 7G:
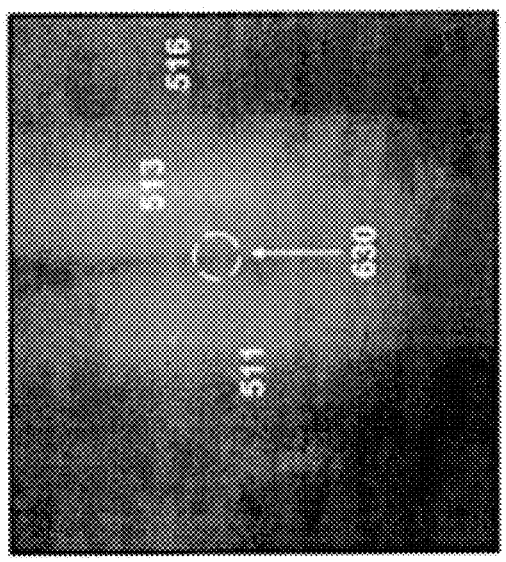
FIG. 7G shows an image roughly corresponding to FIG. 7F as seen through a CCD camera.
Figure 7I:
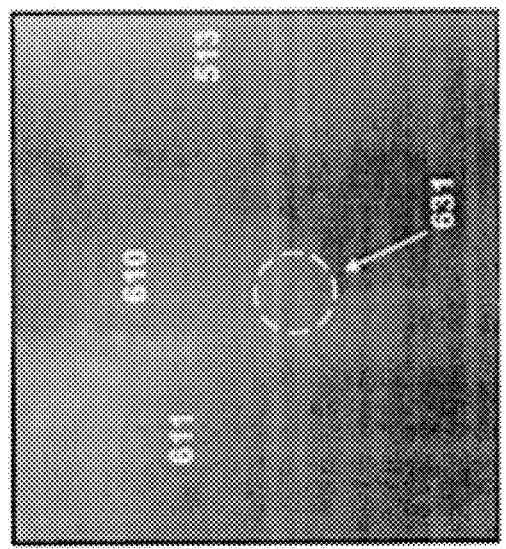
FIG. 7I shows an image roughly corresponding to FIG. 7H as seen through a CCD camera.

Once the operator has advances the distal end of catheter 1 sufficiently close to the ethmoidal bulla 610, the operator articulates the distal end of the catheter 1 in a downward direction and is then able to view the groove 612 between ethmoidal bulla 610 and uncinate process 611 as shown in FIG. 7J. The operator advances the distal end of catheter 1 in this downward articulated state along groove 612 as also shown in FIG. 6J. FIG. 7K is an image as seen through a CCD camera 13 while performing the movement as described with reference to FIG. 7J.

Figure 7L:
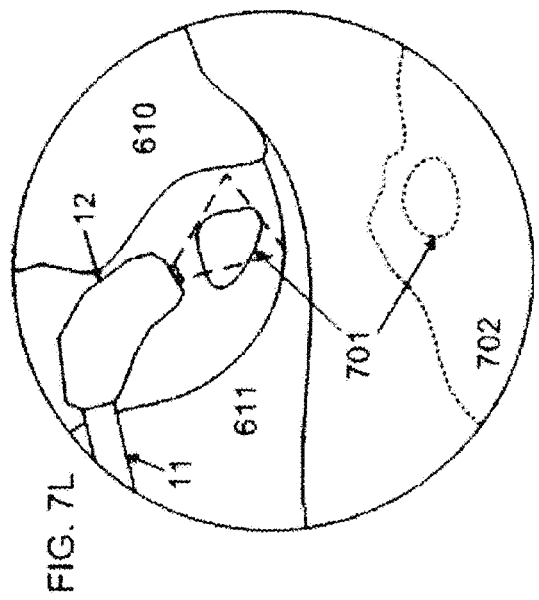
FIG. 7L shows approach of the distal end of the balloon catheter to one of the openings to the ostium of the maxillary sinus.
Figure 7N:
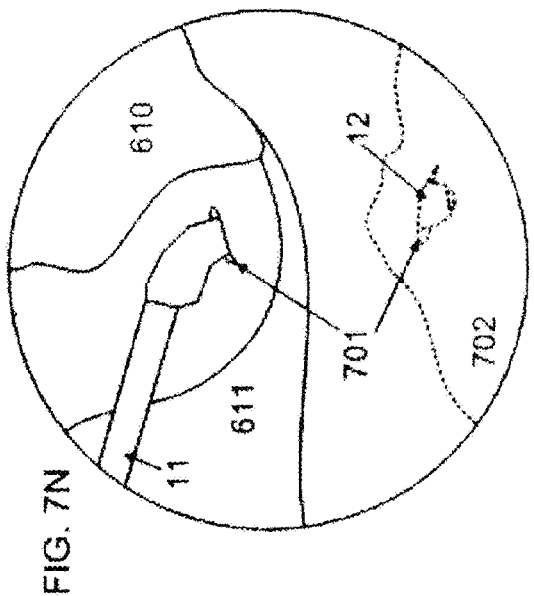
FIG. 7N shows insertion of the distal end of the balloon catheter into the ostium of the maxillary sinus.
Figure 7K:
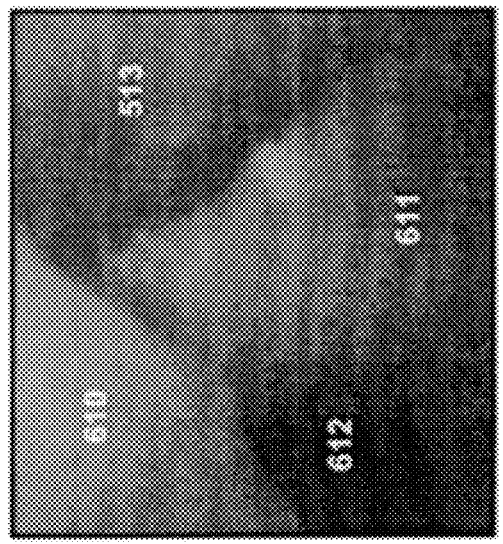
FIG. 7K shows an image roughly corresponding to FIG. 7J as seen through a CCD camera.
Figure 7M:
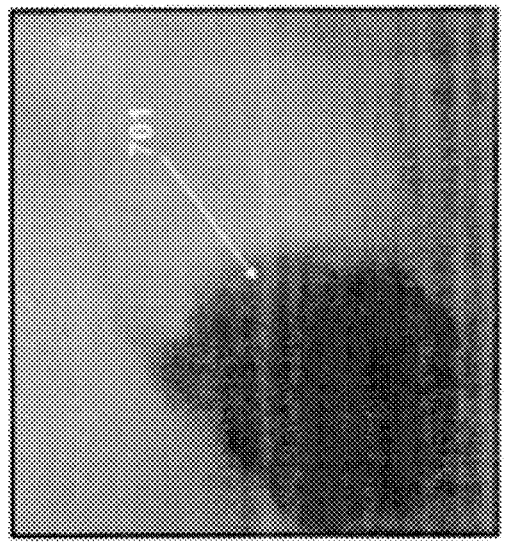
FIG. 7M shows an image roughly corresponding to FIG. 7L as seen through a CCD camera.
Figure 7P:
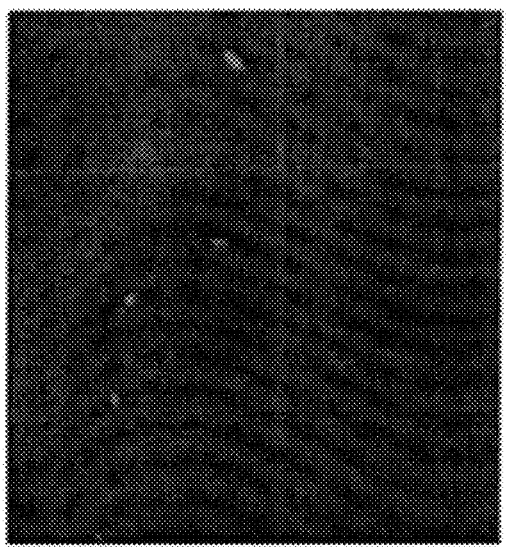
FIG. 7P shows an image roughly corresponding to FIG. 7N as seen through a CCD camera.

The operator advances the distal end of catheter 1 along groove 612 until the opening 701 of the maxillary sinus 702 is visible as shown in FIG. 7L. FIG. 7M is an image as seen through a CCD camera 13 while performing the movement as described with reference to FIG. 7L. Where other openings, sometimes called accessory ostia, other than the desired opening 701 exist in the same general area as opening 701, the operator may need to observe the openings using the CCD camera 13 as shown in FIG. 7L and FIG. 7M in order to identify the correct ostium for insertion. Continuing to advance the distal end of catheter 1 toward the opening 701 of maxillary sinus 702, the operator advances the balloon 12 into the ostium connecting maxillary sinus 702 to the rest of the nasal cavity as shown in FIG. 7N. As depicted, the operator may need to articulate the distal end of catheter 1 as that distal end is advanced through the ostium so that the catheter 1 will continue advancing along the path of that ostium. FIG. 7O is an image as seen through a CCD camera 13 while performing the movement as described with reference to FIG. 7N. In particular, FIG. 7O shows the inside of the maxillary sinus ostium and the opening 701 of the maxillary sinus 702 that exits the maxillary sinus ostium and enters the maxillary sinus 702. As such, the image shows how the operator may view the opening 701 of the maxillary sinus 702 as he advances the distal end of catheter 1 through the maxillary sinus ostium. FIG. 7P is an image as seen through a CCD camera 13 while performing the movement as described with reference to FIG. 7N, wherein the distal end of catheter 1 has been advanced through the maxillary sinus ostium and now is sufficiently advanced into the maxillary sinus 702 so as to allow the operator to view the interior wall of the maxillary sinus 702. In some situations, it may be advantageous to advance the distal end of catheter 1 until it just enters the maxillary sinus 702, and then use the camera advancement control 16 to advance just the CCD camera 13 and LED light 14 further into the maxillary sinus 702 in order to see the interior wall of the maxillary sinus 702 as shown in FIG. 7P.

Figure 7R:
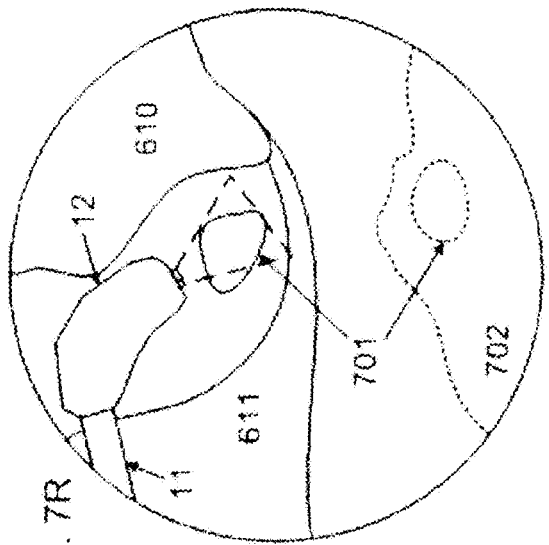
Figure 7O:
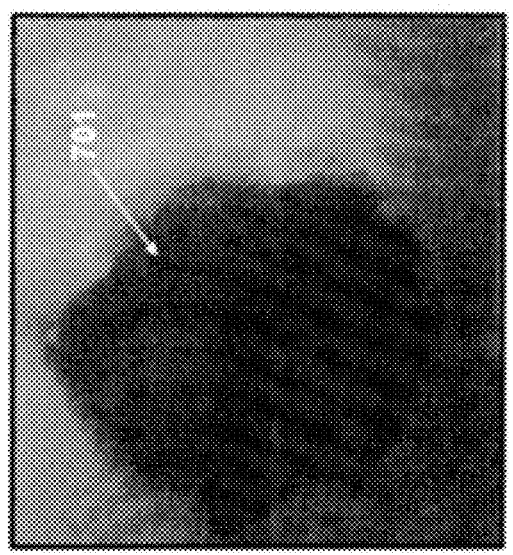
FIG. 7O shows an image roughly corresponding to FIG. 7N as seen through a CCD camera.
Figure 7Q:
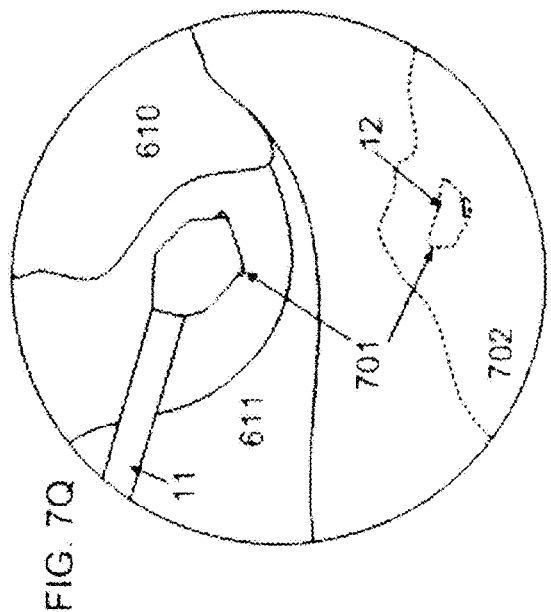
FIG. 7Q shows expansion of the balloon catheter.

Once balloon 12 is positioned between openings 701 of the maxillary sinus 702, the operator changes balloon 12 to its expanded state as shown in FIG. 7Q. This expansion is effective to correct the stenosis of the ostium. Once treatment by means of expansion is complete, the operator returns balloon 12 to its non-expanded state and removes it from the ostium. This removal may require articulation of the distal end of catheter 12 substantially in reverse of the articulation that the operator effectuated to allow the balloon 12 to enter the ostium.

Once the balloon 12 is fully removed from the ostium, the operator can use CCD camera 13 to inspect the ostium in order to verify that the treatment was successful to correct the stenosis of the ostium as shown in FIG. 7R. The operator then removes catheter 1 from the nasal cavity.

According to the method of the present invention as above-described, the expansion body (balloon), particularly the effective expansive section of the expansion body (balloon) can be disposed over substantially the whole length of the stenosed part, so that the whole of the stenosed part can be pushed open when the expansion body (balloon) is expanded. According to the above-mentioned method, therefore, the stenosed part of the natural ostium can be pushed open more assuredly, so that a therapeutic effect on sinusitis can be enhanced. Besides, according to the above-described method, the catheter can be effectively prevented from being advanced excessively into the paranasal sinus cavity, so that safety in treatment of sinusitis can be enhanced. Furthermore, according to the method of the present invention, the expansion body in the inside of the nasal cavity can be positioned easily and accurately, and the stenosed part of the paranasal sinus cavity can be dilated assuredly and easily, by use of a simple device such as an endoscope, without using any special apparatus such as an X-ray apparatus. In addition, the method according to the present invention is a minimally invasive method based on the use of a catheter, which promises less-invasiveness to the patient.

The present invention may be practiced or embodied in still other ways without departing from the spirit or essential character thereof. The preferred embodiments described herein are therefore illustrative and not restrictive, the scope of the invention being indicated by the appended claims and all variations which fall within the meaning of the claims are intended to be embraced therein.

What is claimed is:
1. A method comprising:
   providing a balloon catheter device that includes;
      a selectively bendable portion with a balloon disposed thereon,
      a control device for controlling bending of the selectively bendable portion,
      a camera located at an end of a distal portion of the balloon catheter device such that the camera moves along with movement of the selectively bendable portion by operating the control device, and a camera advancement control configured to control movement of the camera between a non-extended state and an extended state, wherein the camera is located at the end of the distal portion of the balloon catheter device in the non-extended state, wherein the camera is advanced beyond the end of the distal portion of the balloon catheter device in the extended state;

inserting the distal portion into the nostril while the distal portion is straight;

viewing an image provided by the camera;

stopping insertion of the distal portion after the ethmoidal bulla is viewed in the image;

articulating the distal portion in an upward direction to view the opening to the frontal sinus ostium or a downward direction to view the opening to the maxillary sinus ostium using the control device;

inserting the distal portion into the frontal sinus ostium or the maxillary sinus ostium while the distal portion remains in the bent position; and inflating the balloon in the frontal sinus ostium or the maxillary sinus ostium.

2. The method of claim 1 wherein the step of articulating the distal portion is performed so as to bend the distal portion in an upward direction to view the opening to the frontal sinus ostium.

3. The method of claim 2 further comprising placing the balloon catheter device in such a position, before the step of inserting the distal portion into the nostril, so that the distal portion can bend in an upward direction.

4. The method of claim 1 wherein the step of bending the distal portion is performed so as to bend the distal portion in a downward direction to view the opening to the maxillary sinus ostium.

5. The method of claim 4 further comprising placing the balloon catheter device in such a position, before the step of inserting the distal portion into the nostril, so that the distal portion can bend in a downward direction.

6. The method of claim 1 further comprising deflating the balloon in the frontal sinus ostium or maxillary sinus ostium.

7. The method of claim 6 further comprising removing the distal portion from the frontal sinus ostium or maxillary sinus ostium while the distal portion remains in the bent position.

8. The method of claim 7 further comprising viewing the frontal sinus ostium or maxillary sinus ostium using the camera after the steps of inserting the distal portion into the frontal sinus ostium or maxillary sinus ostium, inflating the balloon, deflating the balloon, and removing the distal portion in order to determine whether the method was effective to expand the frontal sinus ostium or maxillary sinus ostium.

9. The method of claim 8 further comprising repeating the steps of inserting the distal portion into the frontal sinus ostium or maxillary sinus ostium and inflating the balloon if the step of viewing the frontal sinus ostium or maxillary sinus ostium resulted in a determination that the method was not effective to expand the frontal sinus ostium or maxillary sinus ostium.

10. The method of claim 1 further comprising viewing the nasal septum and middle turbinate using the camera.

11. The method of claim 10 further comprising advancing the distal portion through the middle nasal meatus.

12. The method of claim 1 further comprising advancing the distal portion while in the bent position along the groove formed between the ethmoidal bulla and the uncinate process.

13. The method of claim 1 wherein the step of stopping insertion of the distal portion is performed when the distal portion appears to have passed the uncinate process and appears to closely approach the ethmoidal bulla as determined by viewing the image using the camera.

14. The method of claim 1 wherein the step of inserting the distal portion into the frontal sinus ostium or maxillary sinus ostium is performed by viewing the inside of the frontal sinus ostium or maxillary sinus ostium using the camera as the distal portion is advanced through the frontal sinus ostium or maxillary sinus ostium, and stopping insertion of the distal portion into the frontal sinus ostium or maxillary sinus ostium when an inside of the frontal sinus ostium or maxillary sinus ostium is no longer visible using the camera.

15. The method of claim 1 wherein the selectively bendable portion only articulates on a single plane and in a single direction from a non-articulated position.

16. The method of claim 1 further comprising approaching the distal end of the balloon catheter device to the ethmoidal bulla until nearly touching it, then articulating the selectively bendable portion.

* * * * *